(12) United States Patent
Cheresh et al.

(10) Patent No.: US 7,585,841 B2
(45) Date of Patent: Sep. 8, 2009

(54) METHODS AND COMPOSITIONS USEFUL FOR MODULATION OF ANGIOGENESIS USING TYROSINE KINASE SRC

(75) Inventors: David A. Cheresh, Encinitas, CA (US); Brian Eliceiri, Carlsbad, CA (US); Pamela L. Schwartzberg, Bethesda, MD (US)

(73) Assignees: The Scripps Research Institute, La Jolla, CA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/230,995

(22) Filed: Sep. 19, 2005

(65) Prior Publication Data

US 2006/0009412 A1 Jan. 12, 2006

Related U.S. Application Data

(62) Division of application No. 09/701,500, filed as application No. PCT/US99/11780 on May 28, 1999, now abandoned.

(60) Provisional application No. 60/087,220, filed on May 29, 1998.

(51) Int. Cl.
*A61K 38/00* (2006.01)
(52) U.S. Cl. ........................................................ 514/12
(58) Field of Classification Search .................. 514/12; 424/94.5
See application file for complete search history.

*Primary Examiner*—Maryam Monshipouri
(74) *Attorney, Agent, or Firm*—Olson & Cepuritis, Ltd.

(57) ABSTRACT

The present invention describes methods for modulating angiogenesis in tissues using Src protein, modified Src protein, and nucleic acids encoding for such. Particularly the invention describes methods for inhibiting angiogenesis using an inactive Src protein, or nucleic acids encoding therefor, or for potentiating angiogenesis using an active Src protein, or nucleic acids encoding therefor. The invention also describes the use of gene delivery systems for providing nucleic acids encoding for the Src protein, or modified forms thereof.

10 Claims, 10 Drawing Sheets

CHICKEN c-SRC cDNA (SEQ ID NO:2)

```
   1 tctgacaccc atctgtctgt ctgtctgtgt gctgcaggag ctgagctgac tctgctgtgg
  61 cctcgcgtac cactgtggcc aggcggtagc tgggacgtgc agcccaccac catggggagc
 121 agcaagagca agcccaagga ccccagccag cgccggcgca gcctggagcc acccgacagc
 181 acccaccacg ggggattccc agcctcgcag accccccaaca agacagcagc ccccgacacg
 241 caccgcaccc ccagccgctc ctttgggacc gtggccaccg agcccaagct cttcggggggc
 301 ttcaacactt ctgacaccgt tacgtcgccg cagcgtgccg gggcactggc tggcggcgtc
 361 accactttcg tggctctcta cgactacgag tcccggactg aaacggactt gtccttcaag
 421 aaaggagaac gcctgcagat tgtcaacaac acggaaggtg actggtggct ggctcattcc
 481 ctcactacag gacagacggg ctacatcccc agtaactatg tcgcgccctc agactccatc
 541 caggctgaag agtggtactt tggggaagatc actcgtcggg agtccgagcg gctgctgctc
 601 aaccccgaaa accccggggg aaccttcttg gtccgggaga gcgagacgac aaaaggtgcc
 661 tattgcctct ccgtttctga ctttgacaac gccaaggggc tcaatgtgaa gcactacaag
 721 atccgcaagc tggacagcgg cggcttctac atcacctcac gcacacagtt cagcagcctg
 781 cagcagctgg tggcctacta ctccaaacat gctgatggct tgtgccaccg cctgaccaac
 841 gtctgcccca cgtccaagcc ccagacccag ggactcgcca aggacgcgtg ggaaatcccc
 901 cgggagtcgc tgcggctgga ggtgaagctg gggcagggct gctttggaga ggtctggatg
 961 gggacctgga acggcaccac cagagtggcc ataaagactc tgaagcccgg caccatgtcc
1021 ccggaggcct tcctgcagga agcccaagtg atgaagaagc tccggcatga aagctggtt
1081 cagctgtacg cagtggtgtc ggaagagccc atctacatcg tcactgagta catgagcaag
1141 gggagcctcc tggatttcct gaagggagag atgggcaagt acctgcggct gccacagctc
1201 gtcgatatgg ctgctcagat tgcatccggc atggcctatg tggagaggat gaactacgtg
1261 caccgagacc tgcgggcggc caacatcctg gtgggggaga acctggtgtg caaggtggct
1321 gactttgggc tggcacgcct catcgaggac aacgagtaca cagcacggca aggtgccaag
1381 ttccccatca gtggacagc ccccgaggca gccctctatg gccggttcac catcaagtcg
1441 gatgtctggt ccttcggcat cctgctgact gagctgacca ccaagggccg ggtgccatac
1501 ccagggatgg tcaacaggga ggtgctggac caggtggaga ggggctaccg catgccctgc
1561 ccgcccgagt gccccgagtc gctgcatgac ctcatgtgcc agtgctggcg gagggaccct
1621 gaggagcggc ccactttga gtacctgcag gccttcctgg aggactactt cacctcgaca
1681 gagccccagt accagcctgg agagaaccta taggcctgga gctcctcctg gaccagaggc
1741 ctcgctgtgg ggtacaggg
```

FIG. 1

CHICKEN cSRC ENCODED PROTEIN (SEQ ID NO:3)

MGSSKSKPKDPSQRRRSLEPPDSTHHGGFPASQTPNKTAA

PDTHRTPSRSFGTVATEPKLFGGFNTSDTVTSPQRAGALA

GGVTTFVALYDYESRTETDLSFKKGERLQIVNNTEGDWWL

AHSLTTGQTGYIPSNYVAPSDSIQAEEWYFGKITRRESER

LLLNPENPRGTFLVRESETTKGAYCLSVSDFDNAKGLNVK

HYKIRKLDSGGFYITSRTQFSSLQQLVAYYSKHADGLCHR

LTNVCPTSKPQTQGLAKDAWEIPRESLRLEVKLGQGCFGE

VWMGTWNGTTRVAIKTLKPGTMSPEAFLQEAQVMKKLRHE

KLVQLYAVVSEEPIYIVTEYMSKGSLLDFLKGEMGKYLRL

PQLVDMAAQIASGMAYVERMNYVHRDLRAANILVGENL

VCKVADFGLARLIEDNEYTARQGAKFPIKWTAPEAALYGR

FTIKSDVWSFGILLTELTTKGRVPYPGMVNREVLDQVERG

YRMPCPPECPESLHDLMCQCWRRDPEERPTFEYLQAFLE

DYFTSTEPQYQPGENL

FIG. 2

HUMAN c-SRC cDNA (SEQ ID NO:4)

```
   1 gcgccgcgtc ccgcaggccg tgatgccgcc cgcgcggagg tggcccggac cgcagtgccc
  61 caagagagct ctaatggtac caagtgacag gttggcttta ctgtgactcg gggacgccag
 121 agctcctgag aagatgtcag caatacaggc cgcctggcca tccggtacag aatgtattgc
 181 caagtacaac ttccacggca ctgccgagca ggacctgccc ttctgcaaag gagacgtgct
 241 caccattgtg gccgtcacca aggacccaa ctggtacaaa gccaaaaaca aggtgggccg
 301 tgagggcatc atcccagcca actacgtcca gaagcgggag ggcgtgaagg cgggtaccaa
 361 actcagcctc atgccttggt tccacggcaa gatcacacgg agcaggctg agcggcttct
 421 gtacccgccg gagacaggcc tgttcctggt gcgggagagc accaactacc ccggagacta
 481 cacgctgtgc gtgagctgcg acggcaaggt ggagcactac cgcatcatgt accatgccag
 541 caagctcagc atcgacgagg aggtgtactt tgagaacctc atgcagctgg tggagcacta
 601 cacctcagac gcagatggac tctgtacgcg cctcattaaa ccaaaggtca tggagggcac
 661 agtggcggcc caggatgagt tctaccgcag cggctgggcc ctgaacatga aggagctgaa
 721 gctgctgcag accatcggga aggggggagtt cggagacgtg atgctgggcg attaccgagg
 781 gaacaaagtc gccgtcaagt gcattaagaa cgacgccact gcccaggcct tcctggctga
 841 agcctcagtc atgacgcaac tgcggcatag caacctggtg cagctcctgg gcgtgatcgt
 901 ggaggagaag ggcgggctct acatcgtcac tgagtacatg gccaagggga gccttgtgga
 961 ctacctgcgg tctaggggtc ggtcagtgct gggcggagac tgtctcctca agttctcgct
1021 agatgtctgc gaggccatgg aatacctgga gggcaacaat ttcgtgcatc gagacctggc
1081 tgcccgcaat gtgctggtgt ctgaggacaa cgtggccaag gtcagcgact tggtctcac
1141 caaggaggcg tccagcaccc aggacacggg caagctgcca gtcaagtgga cagcccctga
1201 ggccctgaga gagaagaaat ctccactaa gtctgacgtg tggagtttcg gaatccttct
1261 ctgggaaatc tactcctttg ggcgagtgcc ttatccaaga attccctga aggacgtcgt
1321 ccctcgggtg gagaagggct acaagatgga tgcccccgac ggctgcccgc cgcagtcta
1381 tgaagtcatg aagaactgct ggcacctgga cgccgccatg cggccctcct cctacagct
1441 ccgagagcag cttgagcaca tcaaaaccca cgagctgcac ctgtgacggc tggcctccgc
1501 ctgggtcatg ggcctgtggg gactgaacct ggaagatcat ggacctggtg cccctgctca
1561 ctgggcccga gcctgaactg agcccagcg gctggcggg cctttttcct gcgtcccagc
1621 ctgcacccct ccggccccgt ctctcttgga cccacctgtg gggcctgggg agcccactga
1681 ggggccaggg aggaaggagg ccacggagcg ggaggcagcg ccccaccacg tcgggcttcc
1741 ctggcctccc gccactcgcc ttcttagagt tttattcctt tccttttttg agatttttt
1801 tccgtgtgtt tattttttat tattttcaa gataaggaga aagaaagtac ccagcaaatg
1861 ggcattttac aagaagtacg aatcttattt ttcctgtcct gcccgtgagg gtggggggga
1921 ccgggcccct ctctagggac ccctcgcccc agcctcattc cccattctgt gtcccatgtc
1981 ccgtgtctcc tcggtcgccc cgtgtttgcg cttgaccatg ttgcactgtt tgcatgcgcc
2041 cgaggcagac gtctgtcagg ggcttggatt tcgtgtgccg ctgccacccg cccacccgcc
2101 ttgtgagctg gaattgtaat aaaccacgcc atgaggacac cgccgcccgc ctcggcgctt
2161 cctccaccga aaaaaaaaa aaaaaaa
```

FIG. 3

HUMAN c-SRC ENCODED PROTEIN (SEQ ID NO:5)

MSAIQAAWPSGTECIAKYNFHGTAEQDLPFCKGDVLTIVAVTKD

PNWYKAKNKVGREGIIPANYVQKREGVKAGTKLSLMPWFHGKIT

REQAERLLYPPETGLFLVRESTNYPGDYTLCVSCDGKVEHYRIMY

HASKLSIDEEVYFENLMQLVEHYTSDADGLCTRLIKPKVMEGTVA

AQDEFYRSGWALNMKELKLLQTIGKGEFGDVMLGDYRGNKVAV

KCIKNDATAQAFLAEASVMTQLRHSNLVQLLGVIVEEKGGLYIVTE

YMAKGSLVDYLRSRGRSVLGGDCLLKFSLDVCEAMEYLEGNNFVH

RDLAARNVLVSEDNVAKVSDFGLTKEASSTQDTGKLPVKWTAPEAL

REKKFSTKSDVWSFGILLWEIYSFGRVPYPRIPLKDVVPRVEKGYKM

DAPDGCPPAVYEVMKNCWHLDAAMRPSFLQLREQLEHIKTHELHL

FIG. 4

Effect of RCAS-mediated expression of
Src A on angiogenesis in the chick CAM
FIG. 6A
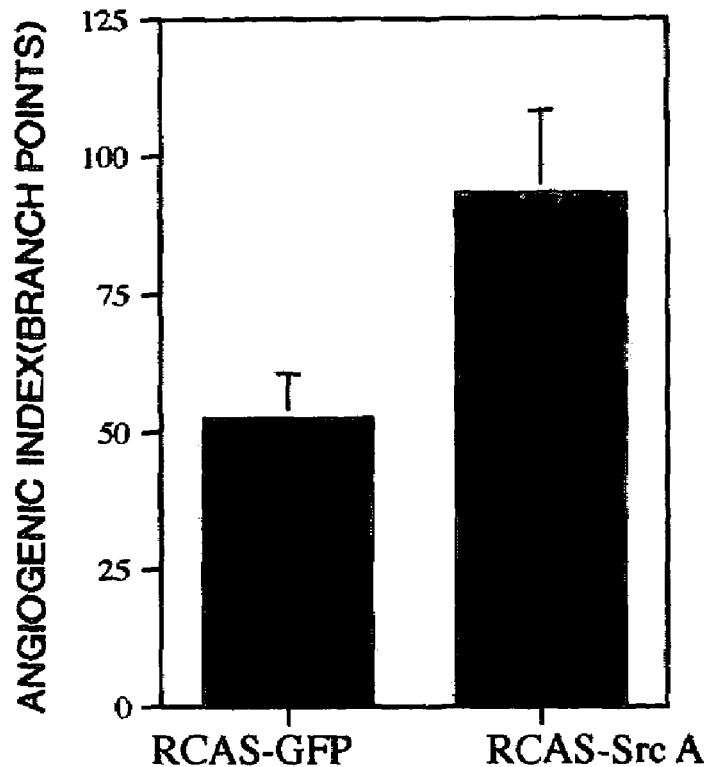
FIG. 6B
 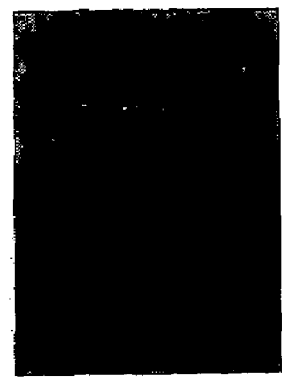
RCAS-GFP       RCAS-Src A

Retroviral expression of Src A activates vascular MAP kinase phosphorylation

I.P.:anti-Src kinase assay — -FAK-GST

Blot: anti-P-Erk — -P-Erk

NT  VEGF  PMA  Src A

Mock

Src A

Selective requirement for Src activity during VEGF, but not bFGF-induced angiogenesis

SEQUENCE LISTING

```
<160> NUMBER OF SEQ ID NOS: 6

<210> SEQ ID NO 1
<211> LENGTH: 11627
<212> TYPE: DNA
<213> ORGANISM: Artificial Sequence
<220> FEATURE:
<223> OTHER INFORMATION: Description of Artificial Sequence:RCASBP(A)
      based on avian sarcoma virus
<220> FEATURE:
<221> NAME/KEY: misc_feature
<222> LOCATION: (7649)..(11258)
<223> OTHER INFORMATION: pBR322 sequences
<220> FEATURE:
<221> NAME/KEY: LTR
<222> LOCATION: (7166)..(7494)
<223> OTHER INFORMATION: upstream
<220> FEATURE:
<221> NAME/KEY: LTR
<222> LOCATION: (1)..(101)
<223> OTHER INFORMATION: upstream (numbering begins at the upstream R)
<220> FEATURE:
<221> NAME/KEY: misc_feature
<222> LOCATION: (11394)..(11623)
<223> OTHER INFORMATION: U3
<220> FEATURE:
<221> NAME/KEY: misc_feature
<222> LOCATION: (1)..(21)
<223> OTHER INFORMATION: R
<220> FEATURE:
<221> NAME/KEY: misc_feature
<222> LOCATION: (22)..(101)
<223> OTHER INFORMATION: U5
<220> FEATURE:
<221> NAME/KEY: misc_feature
<222> LOCATION: (102)..(119)
<220> FEATURE:
<221> NAME/KEY: LTR
<222> LOCATION: (7166)..(7494)
<223> OTHER INFORMATION: downstream
<220> FEATURE:
<221> NAME/KEY: misc_feature
<222> LOCATION: (7166)..(7393)
<223> OTHER INFORMATION: U3
<220> FEATURE:
<221> NAME/KEY: misc_feature
<222> LOCATION: (7394)..(7414)
<223> OTHER INFORMATION: R
<220> FEATURE:
<221> NAME/KEY: misc_feature
<222> LOCATION: (7415)..(7494)
<223> OTHER INFORMATION: U5
<220> FEATURE:
<221> NAME/KEY: misc_feature
<222> LOCATION: (7154)..(7165)
<223> OTHER INFORMATION: PPT
<220> FEATURE:
<221> NAME/KEY: misc_feature
<222> LOCATION: (388)..(391)
<223> OTHER INFORMATION: splice donor (AGGT)
<220> FEATURE:
<221> NAME/KEY: misc_feature
<222> LOCATION: (5074)..(5077)
<223> OTHER INFORMATION: env splice acceptor (AGGC)
<220> FEATURE:
<221> NAME/KEY: misc_feature
<222> LOCATION: (6982)..(6985)
<223> OTHER INFORMATION: ClaI splice acceptor (AGGA)
<220> FEATURE:
<221> NAME/KEY: gene
<222> LOCATION: (372)..(902)
<223> OTHER INFORMATION: gag p19
<220> FEATURE:
<221> NAME/KEY: gene
<222> LOCATION: (909)..(1094)
<223> OTHER INFORMATION: gag p10
```

```
<220> FEATURE:
<221> NAME/KEY: gene
<222> LOCATION: (1095)..(1814)
<223> OTHER INFORMATION: gag p27
<220> FEATURE:
<221> NAME/KEY: gene
<222> LOCATION: (1843)..(2108)
<223> OTHER INFORMATION: gag p12
<220> FEATURE:
<221> NAME/KEY: gene
<222> LOCATION: (2109)..(2480)
<223> OTHER INFORMATION: gag p15
<220> FEATURE:
<221> NAME/KEY: misc_signal
<222> LOCATION: (2481)..(2483)
<223> OTHER INFORMATION: gag stop
<220> FEATURE:
<221> NAME/KEY: gene
<222> LOCATION: (2501)..(4216)
<223> OTHER INFORMATION: pol RT
<220> FEATURE:
<221> NAME/KEY: gene
<222> LOCATION: (4217)..(5185)
<223> OTHER INFORMATION: pol IN
<220> FEATURE:
<221> NAME/KEY: misc_signal
<222> LOCATION: (5186)..(5188)
<223> OTHER INFORMATION: pol stop
<220> FEATURE:
<221> NAME/KEY: gene
<222> LOCATION: (5244)..(6263)
<223> OTHER INFORMATION: env gp85
<220> FEATURE:
<221> NAME/KEY: gene
<222> LOCATION: (6264)..(6878)
<223> OTHER INFORMATION: env gp37
<220> FEATURE:
<221> NAME/KEY: misc_signal
<222> LOCATION: (6879)..(6881)
<223> OTHER INFORMATION: env stop
<220> FEATURE:
<221> NAME/KEY: misc_feature
<222> LOCATION: (7027)
<223> OTHER INFORMATION: ClaI site/ the ClaI site in gag is methylated
      in Dam+ strains and does not cut.

<400> SEQUENCE: 1
gccatttgac cattcaccac attggtgtgc acctgggttg atggccggac cgttgattcc      60
ctgacgacta cgagcacctg catgaagcag aaggcttcat tggtgaccc cgacgtgata     120 gttagggaat agtggtcggc cacagacggg gtggcgatcc tgtctccatc cgtctcgtct     180
atcgggaggc gagttcgatg accctggtgg aggggctgc ggcttaggga ggcagaagct     240
gagtaccgtc ggagggagct ccagggcccg gagcgactga ccctgccga gaactcagag     300 ggtcgtcgga agacggagag tgagcccgac gaccacccca ggcacgtctt tggtcggcct     360
gcggatcaag catggaagcc gtcattaagg tgatttcgtc cgcgtgtaaa acctattgcg     420
ggaaaatctc tccttctaag aaggaaatcg gggccatgtt gtccctgtta caaaggaag     480 ggttgcttat gtctccctca gatttatatt ctccggggtc ctgggatccc atcactgcgg     540
cgctctccca gcgggcaatg gtacttggaa atcgggaga gttaaaaacc tggggattgg     600
tttggggggc attgaaggcg gctcgagagg aacaggttac atctgagcaa gcaaagtttt     660
ggttgggatt aggggaggg agggtctctc ccccaggtcc ggagtgcatc gagaaaccag     720
ctacggagcg gcgaatcgac aaaggggagg aggtgggaga acaactgtg cagcgagatg     780 cgaagatggc gccagaggaa gcggccacac ctaaaaccgt tggcacatcc tgctatcatt     840
gcggaacagc tgttgctgc aattgcgcca ccgccacagc ctcggcccct cctccccctt     900
atgtggggag tggtttgtat ccttccctgg cggggggtggg agagcagcag ggccaggag     960
```

```
ataacacgtc tcggggggcg gagcagccaa gggaggagcc agggcacgcg ggtcaggccc    1020
ctgggccggc cctgactgac tgggcaaggg taagggagga gcttgcgagt actggtccgc    1080
ccgtggtggc catgcctgta gtgattaaga cagagggacc cgcctggacc cctctggagc    1140
caaaattgat cacaagactg gctgatacgg tcaggaccaa gggcttacga tccccgatca    1200
ctatggcaga agtggaagcg ctcatgtcct ccccgttgct gccgcatgac gtcacgaatc    1260
taatgagagt gattttagga cctgccccat atgccttatg gatggacgct tggggagtcc    1320
aactccagac ggttatagcg gcagccactc gcgaccccg acacccagcg aacggtcaag     1380
ggcgggggga acggactaac ttggatcgat taaagggctt agctgatggg atggtgggca    1440
acccacaggg tcaggccgca ttattaagac cggggaatt ggttgctatt acggcgtcgg     1500
ctctccaggc gtttagagaa gttgcccggc tggcggaacc tgcaggtcca tgggcggaca    1560
tcacgcaggg accatctgag tcctttgttg attttgccaa tcggcttata aaggcggttg    1620
aggggtcaga tctcccgcct tccgcgcggg ctccggtgat cattgactgc tttaggcaga    1680
agtcacagcc agatattcag cagcttatac gggcagcacc ctccacgctg accaccccag    1740
gagagataat caaatatgtg ctagacaggc agaagattgc ccctcttacg gatcaaggca    1800
tagccgcggc catgtcgtct gctatccagc ccttagttat ggcagtagtc aatagagaga    1860
gggatggaca aactgggtcg ggtggtcgtg cccgagggct ctgctacact tgtggatccc    1920
cgggacatta tcaggcacag tgcccgaaaa aacgaaagtc aggaaacagc cgtgagcgat    1980
gtcagctgtg tgacgggatg ggacacaacg ctaaacagtg taggaagcgg gatggcaacc    2040
agggccaacg cccaggaaga ggtctctctt cggggccgtg gcccggccct gagcagcctg    2100
ccgtctcgtt agcgatgaca atggaacata agatcgccc cttggttagg gtcattctga     2160
ctaacactgg gagtcatcca gtcaaacaac gttcggtgta tatcaccgcg ctgttggact    2220
ccggagcgga catcactatt atttcggagg aggattggcc tactgattgg ccggtggtgg    2280
acaccgcgaa cccacagatc catggcatag gaggggaat tcccatgcga aaatcccggg     2340
atatgataga ggtgggggtt attaaccgag acgggtcgtt ggagcgaccc ctgctcctct    2400
tccccgcagt cgctatggtt agagggagta cctaggaag agattgtctg cagggcctag     2460
ggctccgctt gacaaattta tagggagggc cactgttctc actgttgcgc tacatctggc    2520
tattccgctc aaatggaagc cagaccgcac gcctgtgtgg attgaccagt ggcccctccc    2580
tgaaggtaaa cttgtaggcc taacgcaatt agtggaaaaa gaattacagt taggacatat    2640
agagccctca cttagttgtt ggaacacacc tgttttcgt gatccggaag gcttccgggt     2700
cttatcgctt attgcatgat ttgcgcgctg ttaacgccaa gcttgtccct ttggggccg     2760 tccaacaggg ggcgccagtt ctctccgcgc tcccgcgtgg ctggcccctg atggtcctag    2820
acctcaagga ttgcttcttt tctatccctc ttgcggaaca agatcgcgaa gcttttgcat    2880
ttacgctccc ctctgtgaat aaccaggccc ccgctcgaag attccaatgg aaggtcttgc    2940
cccaagggat gacctgttct cccactatct gtcagttggt agtgggtcag gtgctcgagc    3000
ccttgcgact caagcaccca gctctgcgca tgttgcatta tatggacgat cttttgctag    3060
ccgcctcaag tcatgatggg ttggaagcgg caggggaagga ggttatcggt acattggaaa   3120
gagccgggtt cactatttcg ccggataaga tccagaggga gccggagta caatatcttg     3180 ggtacaagtt aggcagtacg tatgtagcac ccgtaggctt ggtagcagaa cccaggatag    3240
ccaccttgtg ggatgttcaa aagctggtgg ggtcacttca gtggcttcgc ccagcgttag    3300
```

```
ggatcccgcc acgactgatg ggtcccttttt atgagcagtt acgagggtca gatcctaacg    3360
aggcgaggga atggaatcta gacatgaaaa tggcctggag agagatcgta cagcttagca    3420
ctactgctgc cttggaacga tgggaccctg cccagcctct ggaaggagcg tcgctagat     3480 gtgaacaggg ggcaataggg gtcctgggac agggactgtc cacacaccca aggccatgtt    3540
tgtggttatt ctccacccaa cccaccaagg cgtttactgc ttggttagaa gtgctcaccc    3600
ttttgattac taagctacgc gcttcggcag tgcgaacctt tggcaaggag gttgatatcc    3660
tcctgttgcc tgcatgcttc cgggaggacc ttccgctccc ggaggggatc ctgttagcac    3720 ttaggggggtt tgcaggaaaa atcaggagta gtgcacgcc atctattttt gacattgcgc     3780
gtccactgca tgtttctctg aaagtgaggg ttaccgacca ccctgtgccg ggacccactg    3840
tctttaccga cgcctcctca agcacccata aggggtggt agtctggagg gagggcccaa    3900
ggtgggagat aaaagaaata gttgatttgg gggcaagtgt acaacaactg gaggcacgcg    3960
ctgtggccat ggcacttctg ctgtggccga caacgcccac taatgtagtg actgactctg    4020
cgtttgttgc gaaaatgtta ctcaagatgg gacaggaggg agtcccgtct acagcggcgg    4080 ctttttatttt agaggatgcg ttaagccaaa ggtcagccat ggccgccgtt ctccacgtgc    4140
ggagtcattc tgaagtgcca gggtttttca cagaaggaaa tgacgtggca gatagccaag    4200
ccacctttca agcgtatccc ttgagagagg ctaaagatct tcataccgct ctccatattg    4260 gacccccgcgc gctatccaaa gcgtgtaata tatctatgca gcaggctagg gaggttgttc    4320
agacctgccc gcattgtaat tcagcccctg cgttggaggc cggggtaaac cctagggggtt    4380 tgggaccccct acagatatgg cagacagact ttacgcttga gcctagaatg gctccccgtt    4440
cctggctcgc tgttactgtg gacaccgcct catcagcgat agtcgtaact cagcatggcc    4500
gtgttacatc ggttgctgca caacatcatt gggccacggc tatcgccgtt tgggaagac     4560 caaaggccat aaaaacagat aacgggtcct gcttcacgtc cagatccacg cgagagtggc    4620
tcgcgagatg ggggatagca cacaccaccg ggattccggg aaattcccag ggtcaagcta    4680
tggtagagcg ggccaaccgg ctcctgaaag ataagatccg tgtgctcgcg gagggggacg    4740
gctttatgaa aagaatcccc accagcaaac agggggaact attagccaag gcaatgtatg    4800
ccctcaatca ctttgagcgt ggtgaaaaca caaaaacacc gatacaaaaa cactggagac    4860
ctaccgttct tacagaagga ccccccggtta aaatacgaat agagacaggg gagtgggaaa    4920
aaggatggaa cgtgctggtc tggggacgag gttatgccgc tgtgaaaaac agggacactg    4980
ataaggttat ttgggtaccc tctcggaaag ttaaaccgga tgtcacccaa aaggatgagg    5040
tgactaagaa agatgaggcg agccctcttt ttgcaggcat ttctgactgg atacccctggg    5100 aagacgagca agaaggactc caaggagaaa ccgctagcaa caagcaagaa agacccggag    5160 aagacacccct tgctgccaac gagagttaat tatattctca ttattggtgt cctggtcttg    5220
tgtgaggtta cgggggtaag agctgatgtc cacttactcg agcagccagg gaacctttgg    5280
attacatggg ccaaccgtac aggccaaacg gattttgcc tctctacaca gtcagccacc    5340
tccccttttc aaacatgttt gataggtatc ccgtcccctta tttccgaggg tgattttaag    5400
ggatatgttt ctgatacaaa ttgcaccacc ttgggaactg atcggttagt ctcgtcagcc    5460
gactttactg gcggacctga caacagtacc accctcactt atcggaaggt ctcatgcttg    5520
ttgttaaagc tgaatgtctc tatgtgggat gagccacctg aactacagct gttaggttcc    5580
cagtctctcc ctaacattac taatattgct cagatttccg gtataaccgg gggatgcgta    5640
ggcttcagac cacaagggggt tccttggtat ctaggttggt ctagacagga ggccacgcgg    5700
```

```
tttctcctta gacacccctc tttctctaaa tccacggaac cgtttacagt ggtgacagcg    5760
gataggcaca atcttttat ggggagtgag tactgcggtg catatggcta cagattttgg    5820
aacatgtata actgctcaca ggtggggcgg cagtaccgct gtggtaatgc gcgcacgccc    5880
cgcacgggtc ttcctgaaat ccagtgtaca aggagaggag gcaaatgggt taatcaatca    5940
caggaaatta atgagtcgga gccgttcagc tttacggtga actgtacagc tagtagtttg    6000
ggtaatgcca gtgggtgttg cggaaaagca ggcacgattc tcccgggaaa gtgggtcgac    6060
agcacacaag gtagtttcac caaaccaaaa gcgctaccac ccgcaatttt cctcatttgt    6120
ggggatcgcg catggcaagg aattcccagt cgtccggtag ggggcccctg ctatttaggc    6180
aagcttacca tgttagcacc taagcataca gatattctca aggtgcttgt caattcatcg    6240
cggacaggta taagacgtaa acgaagcacc tcacacctgg atgatacatg ctcagatgaa    6300
gtgcagcttt gggtcctac agcaagaatc tttgcatcta tcctagcccc ggggtagca    6360 gctgcgcaag ccttaagaga aattgagaga ctagcctgtt ggtccgttaa acaggctaac    6420
ttgacaacat cactcctcgg ggacttattg gatgatgtca cgagtattcg acacgcggtc    6480
ctgcagaacc gagcggctat tgacttcttg ctcctagctc acggccatgg ctgtgaggac    6540
gttgccggaa tgtgctgttt caatttgagt gatcagagtg agtctataca gaagaagttc    6600
cagctaatga aggaacatgt caataagatc ggcgtggata gcgacctaat tggaagttgg    6660
ctgcgaggac tattcggggg aataggagaa tgggccgttc atttgctgaa aggactgctt    6720
ttggggcttg tagttatttt gttgctagta gtgtgcctgc cttgccttt gcaaatgtta    6780 tgcggtaata ggagaaagat gattaataac tccatcagct accacacgga atataagaag    6840
ctgcaaaagg cctgtgggca gcctgaaagc agaaatagtat aaggcagtac atgggtggtg    6900
gtatagcgct tgcgagtcca tcgagcaagg caggaaagac agctattggt aattgtgaaa    6960
tacgcttttg tctgtgtgct gcaggagctg agctgactct gctggtggcc tcgcgtacca    7020
ctgtggcatc gatgcgatgt acgggccaga tatacgcgta tctgagggga ctagggtgtg    7080
tttaggcgaa aagcggggct tcggttgtac gcggttagga gtccccttag gatatagtag    7140
tttcgctttt gcatagggag ggggaaatgt agtcttatgc aatactcttg tagtcttgca    7200
acatggtaac gatgagttag caacatgcct tacaaggaga gaaaaagcac cgtgcatgcc    7260
gattggtgga agtaaggtgg tacgatcgtg ccttattagg aaggcaacag acgggtctga    7320
catggattgg acgaaccact gaattccgca ttgcagagat attgtattta agtgcctagc    7380
tcgatacaat aaacgccatt tgaccattca ccacattggt gtgcacctgg gttgatggcc    7440
ggaccgttga ttccctgacg actacgagca cctgcatgaa gcagaaggct tcatttggtg    7500
accccgacgt gatagttagg gaatagtggt cggccacaga cggcgtggcg atcctgtctc    7560
catccgtctc gtctatcggg aggcgacttc gatgaccctg gtggaggggg ctgcggctta    7620
gggaggcaga agctgagtac cgtcggaggg gatccacagg acgggtgtgg tcgccatgat    7680
cgcgtagtcg atagtggctc caagtagcga agcgagcagg actgggcggc ggccaaagcg    7740
gtcggacagt gctccgagaa cgggtgcgca tagaaattgc atcaacgcat atagcgctag    7800
cagcacgcca tagtgactgg cgatgctgtc ggaatggacg atatcccgca agaggcccgg    7860
cagtaccggc ataaccaagc ctatgcctac agcatccagg gtgacggtgc cgaggatgac    7920
gatgagcgca ttgttagatt tcatacacgg tgcctgactg cgttagcaat ttaactgtga    7980
taaactaccg cattaaagct ccaaacttgg ctgtttcctg tgtgaaattg ttatccgctc    8040
```

```
acaattccac acattatacg agccggaagc ataaagtgta aaacctgggg tgcctaatga    8100
gtgagaattc ttgaagacga aagggcctcg tgatacgcct atttttatag gttaatgtca    8160
tgataataat ggtttcttag acgtcaggtg gcacttttcg gggaaatgtg cgcggaaccc    8220
ctatttgttt attttttctaa atacattcaa atatgtatcc gctcatgaga caataaccct    8280
gataaatgct tcaataatat tgaaaaagga gagtatgag tattcaacat ttccgtgtcg    8340
cccttattcc cttttttgcg gcattttgcc ttcctgtttt tgctcaccca gaaacgctgg    8400
tgaaagtaaa agatgctgaa gatcagttgg gtgcacgagt gggttacatc gaactggatc    8460
tcaacagcgg taagatcctt gagagttttc gccccgaaga acgttttcca atgatgagca    8520
cttttaaagt tctgctatgt ggcgcggtat tatcccgtgt tgacgccggg caagagcaac    8580
tcggtcgccg catacactat tctcagaatg acttggttga gtactcacca gtcacagaaa    8640
agcatcttac ggatggcatg acagtaagag aattatgcag tgctgccata accatgagtg    8700
ataacactgc ggccaactta cttctgacaa cgatcgagg accgaaggag ctaaccgctt    8760
ttttgcacaa catgggggat catgtaactc gccttgatcg ttgggaaccg gagctgaatg    8820
aagccatacc aaacgacgag cgtgacacca cgatgcctgc agcaatggca acaacgttgc    8880
gcaaactatt aactggcgaa ctacttactc tagcttcccg gcaacaatta atagactgga    8940
tggaggcgga taaagttgca ggaccacttc tgcgctcggc ccttccggct ggctggttta    9000
ttgctgataa atctggagcc ggtgagcgtg ggtctcgcgg tatcattgca gcactggggc    9060
cagatggtaa gccctcccgt atcgtagtta tctacacgac ggggagtcag gcaactatgg    9120
atgaacgaaa tagacagatc gctgagatag gtgcctcact gattaagcat tggtaactgt    9180
cagaccaagt ttactcatat atactttaga ttgatttaaa acttcatttt taatttaaaa    9240
ggatctaggt gaagatcctt tttgataatc tcatgaccaa aatcccttaa cgtgagtttt    9300
cgttccactg agcgtcagac cccgtagaaa agatcaaagg atcttcttga gatcctttt    9360
ttctgcgcgt aatctgctgc ttgcaaacaa aaaaaccacc gctaccagcg gtggtttgtt    9420
tgccggatca agagctacca actctttttc cgaaggtaac tggcttcagc agagcgcaga    9480
taccaaatac tgtccttcta gtgtagccgt agttaggcca ccacttcaag aactctgtag    9540
caccgcctac atacctcgct ctgctaatcc tgttaccagt ggctgctgcc agtggcgata    9600
agtcgtgtct taccgggttg gactcaagac gatagttacc ggataaggcg cagcggtcgg    9660
gctgaacggg gggttcgtgc acacagccca gcttggagcg aacgacctac accgaactga    9720
gatacctaca gcgtgagcta tgagaaagcg ccacgcttcc cgaagggaga aaggcggaca    9780
ggtatccggt aagcggcagg gtcggaacag gagagcgcac gagggagctt ccagggggaa    9840
acgcctggta tctttatagt cctgtcgggt ttcgccacct ctgacttgag cgtcgatttt    9900
tgtgatgctc gtcagggggg cggagcctat ggaaaaacgc cagcaacgcg gcctttttac    9960
ggttcctggc cttttgctgg ccttttgctc acatgttctt tcctgcgtta tcccctgatt   10020
ctgtggataa ccgtattacc gcctttgagt gagctgatac cgctcgccgc agccgaacga   10080
ccgagcgcag cgagtcagtg agcgaggaag cggaagagcg cctgatgcgg tattttctcc   10140
ttacgcatct gtgcggtatt tcacaccgca tatggtgcac tctcagtaca atctgctctg   10200
atgccgcata gttaagccag tatacactcc gctatcgcta cgtgactggg tcatggctgc   10260
gccccgacac ccgccaacac ccgctgacgc gccctgacgg gcttgtctgc tcccggcatc   10320
cgcttacaga caagctgtga ccgtctccgg gagctgcatg tgtcagaggt tttcaccgtc   10380
atcaccgaaa cgcgcgaggc agctgcggta aagctcatca gcgtggtcgt gaagcgattc   10440
```

-continued

```
acagatgtct gcctgttcat ccgcgtccag ctcgttgagt ttctccagaa gcgttaatgt   10500
ctggcttctg ataaagcggg ccatgttaag ggcggttttt tcctgtttgg tcacttgatg   10560
cctccgtgta aggggaatt  tctgttcatg ggggtaatga taccgatgaa acgagagagg   10620
atgctcacga tacgggttac tgatgatgaa catgcccggt tactggaacg ttgtgagggt   10680
aaacaactgg cggtatggat gcggcgggac cagagaaaaa tcactcaggg tcaatgccag   10740
cgcttcgtta atacagatgt aggtgttcca cagggtagcc agcagcatcc tgcgatgcag   10800
atccggaaca taatggtgca gggcgctgac ttccgcgttt ccagacttta cgaaacacgg   10860
aaaccgaaga ccattcatgt tgttgctcag gtcgcagacg ttttgcagca gcagtcgctt   10920
cacgttcgct cgcgtatcgg tgattcattc tgctaaccag taaggcaacc ccgccagcct   10980
agccgggtcc tcaacgacag gagcacgatc atgagcaccc gtggccagga cccaacgctg   11040
cccgagatgc gccgcgtgcg gctgctggag atggcggacg cgatggatat gttctgccaa   11100
gggttggttt gcgcattcac agttctccgc aagaattgat tggctccaat tcttggagtg   11160
gtgaatccgt tagcgaggtg ccgccggctt ccattcaggt cgaggtggcc cggctccatg   11220
caccgcgacg caacgcgggg aggcagacaa ggtatagggc ggcgatgcga tgtacgggcc   11280
agatatacgc gtatctgagg ggactagggt gtgtttaggc gaaaagcggg gcttcggttg   11340
tacgcggtta ggagtcccct taggatatag tagtttcgct tttgcatagg gaggggaaa   11400 tgtagtctta tgcaatactc ttgtagtctt gcaacatggt aacgatgagt tagcaacatg   11460
ccttacaagg agagaaaaag caccgtgcat gccgattggt ggaagtaagg tggtacgatc   11520
gtgccttatt aggaaggcaa cagacgggtc tgacatggat tggacgaacc actgaattcc   11580
gcattgcaga gatattgtat ttaagtgcct agctcgatac aataaac                11627
```

```
<210> SEQ ID NO 2
<211> LENGTH: 1759
<212> TYPE: DNA
<213> ORGANISM: Chicken
<220> FEATURE:
<221> NAME/KEY: gene
<222> LOCATION: (1)..(1759)
<223> OTHER INFORMATION: chicken c-SRC cDNA
<220> FEATURE:
<221> NAME/KEY: CDS
<222> LOCATION: (112)..(1710)

<400> SEQUENCE: 2
tctgacaccc atctgtctgt ctgtctgtgt gctgcaggag ctgagctgac tctgctgtgg    60
cctcgcgtac cactgtggcc aggcggtagc tgggacgtgc agcccaccac c atg ggg   117
                                                           Met Gly
                                                             1 agc agc aag agc aag ccc aag gac ccc agc cag cgc cgg cgc agc ctg   165
Ser Ser Lys Ser Lys Pro Lys Asp Pro Ser Gln Arg Arg Arg Ser Leu
        5                  10                 15 gag cca ccc gac agc acc cac cac ggg gga ttc cca gcc tcg cag acc   213
Glu Pro Pro Asp Ser Thr His His Gly Gly Phe Pro Ala Ser Gln Thr
    20                 25                 30 ccc aac aag aca gca gcc ccc gac acg cac cgc acc ccc agc cgc tcc   261
Pro Asn Lys Thr Ala Ala Pro Asp Thr His Arg Thr Pro Ser Arg Ser
35                 40                 45                 50 ttt ggg acc gtg gcc acc gag ccc aag ctc ttc ggg ggc ttc aac act   309
Phe Gly Thr Val Ala Thr Glu Pro Lys Leu Phe Gly Gly Phe Asn Thr
                55                 60                 65 tct gac acc gtt acg tcg ccg cag cgt gcc ggg gca ctg gct ggc ggc   357
```

```
Ser Asp Thr Val Thr Ser Pro Gln Arg Ala Gly Ala Leu Ala Gly Gly
             70              75                  80 gtc acc act ttc gtg gct ctc tac gac tac gag tcc cgg act gaa acg       405
Val Thr Thr Phe Val Ala Leu Tyr Asp Tyr Glu Ser Arg Thr Glu Thr
             85              90                  95 gac ttg tcc ttc aag aaa gga gaa cgc ctg cag att gtc aac aac acg       453
Asp Leu Ser Phe Lys Lys Gly Glu Arg Leu Gln Ile Val Asn Asn Thr
    100             105                 110 gaa ggt gac tgg tgg ctg gct cat tcc ctc act aca gga cag acg ggc       501
Glu Gly Asp Trp Trp Leu Ala His Ser Leu Thr Thr Gly Gln Thr Gly
115             120                 125                 130 tac atc ccc agt aac tat gtc gcg ccc tca gac tcc atc cag gct gaa       549
Tyr Ile Pro Ser Asn Tyr Val Ala Pro Ser Asp Ser Ile Gln Ala Glu
                135                 140                 145 gag tgg tac ttt ggg aag atc act cgt cgg gag tcc gag cgg ctg ctg       597
Glu Trp Tyr Phe Gly Lys Ile Thr Arg Arg Glu Ser Glu Arg Leu Leu
            150                 155                 160 ctc aac ccc gaa aac ccc cgg gga acc ttc ttg gtc cgg gag agc gag       645
Leu Asn Pro Glu Asn Pro Arg Gly Thr Phe Leu Val Arg Glu Ser Glu
        165                 170                 175 acg aca aaa ggt gcc tat tgc ctc tcc gtt tct gac ttt gac aac gcc       693
Thr Thr Lys Gly Ala Tyr Cys Leu Ser Val Ser Asp Phe Asp Asn Ala
    180                 185                 190 aag ggg ctc aat gtg aag cac tac aag atc cgc aag ctg gac agc ggc       741
Lys Gly Leu Asn Val Lys His Tyr Lys Ile Arg Lys Leu Asp Ser Gly
195                 200                 205                 210 ggc ttc tac atc acc tca cgc aca cag ttc agc agc ctg cag cag ctg       789
Gly Phe Tyr Ile Thr Ser Arg Thr Gln Phe Ser Ser Leu Gln Gln Leu
                215                 220                 225 gtg gcc tac tac tcc aaa cat gct gat ggc ttg tgc cac cgc ctg acc       837
Val Ala Tyr Tyr Ser Lys His Ala Asp Gly Leu Cys His Arg Leu Thr
            230                 235                 240 aac gtc tgc ccc acg tcc aag ccc cag acc cag gga ctc gcc aag gac       885
Asn Val Cys Pro Thr Ser Lys Pro Gln Thr Gln Gly Leu Ala Lys Asp
        245                 250                 255 gcg tgg gaa atc ccc cgg gag tcg ctg cgg ctg gag gtg aag ctg ggg       933
Ala Trp Glu Ile Pro Arg Glu Ser Leu Arg Leu Glu Val Lys Leu Gly
    260                 265                 270 cag ggc tgc ttt gga gag gtc tgg atg ggg acc tgg aac ggc acc acc       981
Gln Gly Cys Phe Gly Glu Val Trp Met Gly Thr Trp Asn Gly Thr Thr
275                 280                 285                 290 aga gtg gcc ata aag act ctg aag ccc ggc acc atg tcc ccg gag gcc      1029
Arg Val Ala Ile Lys Thr Leu Lys Pro Gly Thr Met Ser Pro Glu Ala
                295                 300                 305 ttc ctg cag gaa gcc caa gtg atg aag aag ctc cgg cat gag aag ctg      1077
Phe Leu Gln Glu Ala Gln Val Met Lys Lys Leu Arg His Glu Lys Leu
            310                 315                 320 gtt cag ctg tac gca gtg gtg tcg gaa gag ccc atc tac atc gtc act      1125
Val Gln Leu Tyr Ala Val Val Ser Glu Glu Pro Ile Tyr Ile Val Thr
        325                 330                 335 gag tac atg agc aag ggg agc ctc ctg gat ttc ctg aag gga gag atg      1173
Glu Tyr Met Ser Lys Gly Ser Leu Leu Asp Phe Leu Lys Gly Glu Met
    340                 345                 350 ggc aag tac ctg cgg ctg cca cag ctc gtc gat atg gct gct cag att      1221
Gly Lys Tyr Leu Arg Leu Pro Gln Leu Val Asp Met Ala Ala Gln Ile
355                 360                 365                 370 gca tcc ggc atg gcc tat gtg gag agg atg aac tac gtg cac cga gac      1269
Ala Ser Gly Met Ala Tyr Val Glu Arg Met Asn Tyr Val His Arg Asp
                375                 380                 385
```

```
ctg cgg gcg gcc aac atc ctg gtg ggg gag aac ctg gtg tgc aag gtg    1317
Leu Arg Ala Ala Asn Ile Leu Val Gly Glu Asn Leu Val Cys Lys Val
        390                 395                 400 gct gac ttt ggg ctg gca cgc ctc atc gag gac aac gag tac aca gca    1365
Ala Asp Phe Gly Leu Ala Arg Leu Ile Glu Asp Asn Glu Tyr Thr Ala
            405                 410                 415 cgg caa ggt gcc aag ttc ccc atc aag tgg aca gcc ccc gag gca gcc    1413
Arg Gln Gly Ala Lys Phe Pro Ile Lys Trp Thr Ala Pro Glu Ala Ala
420                 425                 430 ctc tat ggc cgg ttc acc atc aag tcg gat gtc tgg tcc ttc ggc atc    1461
Leu Tyr Gly Arg Phe Thr Ile Lys Ser Asp Val Trp Ser Phe Gly Ile
435                 440                 445                 450 ctg ctg act gag ctg acc acc aag ggc cgg gtg cca tac cca ggg atg    1509
Leu Leu Thr Glu Leu Thr Thr Lys Gly Arg Val Pro Tyr Pro Gly Met
                455                 460                 465 gtc aac agg gag gtg ctg gac cag gtg gag agg ggc tac cgc atg ccc    1557
Val Asn Arg Glu Val Leu Asp Gln Val Glu Arg Gly Tyr Arg Met Pro
            470                 475                 480 tgc ccg ccc gag tgc ccc gag tcg ctg cat gac ctc atg tgc cag tgc    1605
Cys Pro Pro Glu Cys Pro Glu Ser Leu His Asp Leu Met Cys Gln Cys
                485                 490                 495 tgg cgg agg gac cct gag gag cgg ccc act ttt gag tac ctg cag gcc    1653
Trp Arg Arg Asp Pro Glu Glu Arg Pro Thr Phe Glu Tyr Leu Gln Ala
500                 505                 510 ttc ctg gag gac tac ttc acc tcg aca gag ccc cag tac cag cct gga    1701
Phe Leu Glu Asp Tyr Phe Thr Ser Thr Glu Pro Gln Tyr Gln Pro Gly
515                 520                 525                 530 gag aac cta taggcctgga gctcctcctg gaccagaggc ctcgctgtgg ggtacaggg  1759
Glu Asn Leu <210> SEQ ID NO 3
<211> LENGTH: 533
<212> TYPE: PRT
<213> ORGANISM: Chicken

<400> SEQUENCE: 3

Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
        35                  40                  45

Arg Ser Phe Gly Thr Val Ala Thr Glu Pro Lys Leu Phe Gly Gly Phe
    50                  55                  60

Asn Thr Ser Asp Thr Val Thr Ser Pro Gln Arg Ala Gly Ala Leu Ala
65                  70                  75                  80

Gly Gly Val Thr Thr Phe Val Ala Leu Tyr Asp Tyr Glu Ser Arg Thr
                85                  90                  95

Glu Thr Asp Leu Ser Phe Lys Lys Gly Glu Arg Leu Gln Ile Val Asn
            100                 105                 110

Asn Thr Glu Gly Asp Trp Trp Leu Ala His Ser Leu Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175
```

```
Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
            195                 200                 205

Ser Gly Gly Phe Tyr Ile Thr Ser Arg Thr Gln Phe Ser Ser Leu Gln
            210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
            275                 280                 285

Thr Thr Arg Val Ala Ile Lys Thr Leu Lys Pro Gly Thr Met Ser Pro
            290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Pro Ile Tyr Ile
                325                 330                 335

Val Thr Glu Tyr Met Ser Lys Gly Ser Leu Leu Asp Phe Leu Lys Gly
            340                 345                 350

Glu Met Gly Lys Tyr Leu Arg Leu Pro Gln Leu Val Asp Met Ala Ala
            355                 360                 365

Gln Ile Ala Ser Gly Met Ala Tyr Val Glu Arg Met Asn Tyr Val His
370                 375                 380

Arg Asp Leu Arg Ala Ala Asn Ile Leu Val Gly Glu Asn Leu Val Cys
385                 390                 395                 400

Lys Val Ala Asp Phe Gly Leu Ala Arg Leu Ile Glu Asp Asn Glu Tyr
                405                 410                 415

Thr Ala Arg Gln Gly Ala Lys Phe Pro Ile Lys Trp Thr Ala Pro Glu
            420                 425                 430

Ala Ala Leu Tyr Gly Arg Phe Thr Ile Lys Ser Asp Val Trp Ser Phe
            435                 440                 445

Gly Ile Leu Leu Thr Glu Leu Thr Thr Lys Gly Arg Val Pro Tyr Pro
450                 455                 460

Gly Met Val Asn Arg Glu Val Leu Asp Gln Val Glu Arg Gly Tyr Arg
465                 470                 475                 480

Met Pro Cys Pro Pro Glu Cys Pro Glu Ser Leu His Asp Leu Met Cys
                485                 490                 495

Gln Cys Trp Arg Arg Asp Pro Glu Glu Arg Pro Thr Phe Glu Tyr Leu
            500                 505                 510

Gln Ala Phe Leu Glu Asp Tyr Phe Thr Ser Thr Glu Pro Gln Tyr Gln
            515                 520                 525

Pro Gly Glu Asn Leu
    530

<210> SEQ ID NO 4
<211> LENGTH: 2187
<212> TYPE: DNA
<213> ORGANISM: Homo sapiens
<220> FEATURE:
<221> NAME/KEY: gene
<222> LOCATION: (1)..(2187)
<223> OTHER INFORMATION: human c-SRC cDNA
```

```
<220> FEATURE:
<221> NAME/KEY: CDS
<222> LOCATION: (134)..(1483)

<400> SEQUENCE: 4
gcgccgcgtc  ccgcaggccg  tgatgccgcc  cgcgcggagg  tggcccggac  cgcagtgccc        60
caagagagct  ctaatggtac  caagtgacag  gttggcttta  ctgtgactcg  gggacgccag       120
agctcctgag  aag atg tca gca ata cag gcc gcc tgg cca tcc ggt aca            169
               Met Ser Ala Ile Gln Ala Ala Trp Pro Ser Gly Thr
                 1               5                  10 gaa tgt att gcc aag tac aac ttc cac ggc act gcc gag cag gac ctg            217
Glu Cys Ile Ala Lys Tyr Asn Phe His Gly Thr Ala Glu Gln Asp Leu
         15                  20                  25 ccc ttc tgc aaa gga gac gtg ctc acc att gtg gcc gtc acc aag gac            265
Pro Phe Cys Lys Gly Asp Val Leu Thr Ile Val Ala Val Thr Lys Asp
 30                  35                  40 ccc aac tgg tac aaa gcc aaa aac aag gtg ggc cgt gag ggc atc atc            313
Pro Asn Trp Tyr Lys Ala Lys Asn Lys Val Gly Arg Glu Gly Ile Ile
 45                  50                  55                  60 cca gcc aac tac gtc cag aag cgg gag ggc gtg aag gcg ggt acc aaa            361
Pro Ala Asn Tyr Val Gln Lys Arg Glu Gly Val Lys Ala Gly Thr Lys
                 65                  70                  75 ctc agc ctc atg cct tgg ttc cac ggc aag atc aca cgg gag cag gct            409
Leu Ser Leu Met Pro Trp Phe His Gly Lys Ile Thr Arg Glu Gln Ala
         80                  85                  90 gag cgg ctt ctg tac ccg ccg gag aca ggc ctg ttc ctg gtg cgg gag            457
Glu Arg Leu Leu Tyr Pro Pro Glu Thr Gly Leu Phe Leu Val Arg Glu
         95                 100                 105 agc acc aac tac ccc gga gac tac acg ctg tgc gtg agc tgc gac ggc            505
Ser Thr Asn Tyr Pro Gly Asp Tyr Thr Leu Cys Val Ser Cys Asp Gly
110                 115                 120 aag gtg gag cac tac cgc atc atg tac cat gcc agc aag ctc agc atc            553
Lys Val Glu His Tyr Arg Ile Met Tyr His Ala Ser Lys Leu Ser Ile
125                 130                 135                 140 gac gag gag gtg tac ttt gag aac ctc atg cag ctg gtg gag cac tac            601
Asp Glu Glu Val Tyr Phe Glu Asn Leu Met Gln Leu Val Glu His Tyr
                145                 150                 155 acc tca gac gca gat gga ctc tgt acg cgc ctc att aaa cca aag gtc            649
Thr Ser Asp Ala Asp Gly Leu Cys Thr Arg Leu Ile Lys Pro Lys Val
        160                 165                 170 atg gag ggc aca gtg gcg gcc cag gat gag ttc tac cgc agc ggc tgg            697
Met Glu Gly Thr Val Ala Ala Gln Asp Glu Phe Tyr Arg Ser Gly Trp
        175                 180                 185 gcc ctg aac atg aag gag ctg aag ctg ctg cag acc atc ggg aag ggg            745
Ala Leu Asn Met Lys Glu Leu Lys Leu Leu Gln Thr Ile Gly Lys Gly
        190                 195                 200 gag ttc gga gac gtg atg ctg ggc gat tac cga ggg aac aaa gtc gcc            793
Glu Phe Gly Asp Val Met Leu Gly Asp Tyr Arg Gly Asn Lys Val Ala
205                 210                 215                 220 gtc aag tgc att aag aac gac gcc act gcc cag gcc ttc ctg gct gaa            841
Val Lys Cys Ile Lys Asn Asp Ala Thr Ala Gln Ala Phe Leu Ala Glu
                225                 230                 235 gcc tca gtc atg acg caa ctg cgg cat agc aac ctg gtg cag ctc ctg            889
Ala Ser Val Met Thr Gln Leu Arg His Ser Asn Leu Val Gln Leu Leu
        240                 245                 250 ggc gtg atc gtg gag gag aag ggc ggg ctc tac atc gtc act gag tac            937
Gly Val Ile Val Glu Glu Lys Gly Gly Leu Tyr Ile Val Thr Glu Tyr
        255                 260                 265 atg gcc aag ggg agc ctt gtg gac tac ctg cgg tct agg ggt cgg tca            985
```

```
                Met Ala Lys Gly Ser Leu Val Asp Tyr Leu Arg Ser Arg Gly Arg Ser
                    270                 275                 280 gtg ctg ggc gga gac tgt ctc ctc aag ttc tcg cta gat gtc tgc gag        1033
Val Leu Gly Gly Asp Cys Leu Leu Lys Phe Ser Leu Asp Val Cys Glu
285                 290                 295                 300 gcc atg gaa tac ctg gag ggc aac aat ttc gtg cat cga gac ctg gct        1081
Ala Met Glu Tyr Leu Glu Gly Asn Asn Phe Val His Arg Asp Leu Ala
                305                 310                 315 gcc cgc aat gtg ctg gtg tct gag gac aac gtg gcc aag gtc agc gac        1129
Ala Arg Asn Val Leu Val Ser Glu Asp Asn Val Ala Lys Val Ser Asp
            320                 325                 330 ttt ggt ctc acc aag gag gcg tcc agc acc cag gac acg ggc aag ctg        1177
Phe Gly Leu Thr Lys Glu Ala Ser Ser Thr Gln Asp Thr Gly Lys Leu
        335                 340                 345 cca gtc aag tgg aca gcc cct gag gcc ctg aga gag aag aaa ttc tcc        1225
Pro Val Lys Trp Thr Ala Pro Glu Ala Leu Arg Glu Lys Lys Phe Ser
    350                 355                 360 act aag tct gac gtg tgg agt ttc gga atc ctt ctc tgg gaa atc tac        1273
Thr Lys Ser Asp Val Trp Ser Phe Gly Ile Leu Leu Trp Glu Ile Tyr
365                 370                 375                 380 tcc ttt ggg cga gtg cct tat cca aga att ccc ctg aag gac gtc gtc        1321
Ser Phe Gly Arg Val Pro Tyr Pro Arg Ile Pro Leu Lys Asp Val Val
                385                 390                 395 cct cgg gtg gag aag ggc tac aag atg gat gcc ccc gac ggc tgc ccg        1369
Pro Arg Val Glu Lys Gly Tyr Lys Met Asp Ala Pro Asp Gly Cys Pro
                400                 405                 410 ccc gca gtc tat gaa gtc atg aag aac tgc tgg cac ctg gac gcc gcc        1417
Pro Ala Val Tyr Glu Val Met Lys Asn Cys Trp His Leu Asp Ala Ala
            415                 420                 425 atg cgg ccc tcc ttc cta cag ctc cga gag cag ctt gag cac atc aaa        1465
Met Arg Pro Ser Phe Leu Gln Leu Arg Glu Gln Leu Glu His Ile Lys
        430                 435                 440 acc cac gag ctg cac ctg tgacggctgg cctccgcctg ggtcatgggc               1513
Thr His Glu Leu His Leu
445                 450 ctgtggggac tgaacctgga agatcatgga cctggtgccc ctgctcactg ggcccgagcc      1573
tgaactgagc cccagcgggc tggcgggcct ttttcctgcg tcccagcctg caccctccg       1633 gccccgtctc tcttggaccc acctgtgggg cctggggagc ccactgaggg gccagggagg      1693
aaggaggcca cggagcggga ggcagcgccc caccacgtcg ggcttccctg gcctccgcc       1753 actcgccttc ttagagtttt attcctttcc tttttttgaga tttttttttcc gtgtgtttat    1813 tttttattat tttcaagat aaggagaaag aaagtaccca gcaaatgggc attttacaag       1873
aagtacgaat cttattttc ctgtcctgcc cgtgagggtg ggggggaccg ggcccctctc       1933
tagggacccc tcgcccagc ctcattcccc attctgtgtc ccatgtcccg tgtctcctcg       1993
gtcgccccgt gtttgcgctt gaccatgttg cactgttttgc atgcgcccga ggcagacgtc     2053
tgtcaggggc ttggatttcg tgtgccgctg ccacccgccc acccgccttg tgagatggaa      2113
ttgtaataaa ccacgccatg aggacaccgc cgcccgcctc ggcgcttcct ccaccgaaaa      2173
aaaaaaaaaa aaaa                                                        2187

<210> SEQ ID NO 5
<211> LENGTH: 450
<212> TYPE: PRT
<213> ORGANISM: Homo sapiens

<400> SEQUENCE: 5
```

-continued

```
Met Ser Ala Ile Gln Ala Ala Trp Pro Ser Gly Thr Glu Cys Ile Ala
 1               5                  10                  15

Lys Tyr Asn Phe His Gly Thr Ala Glu Gln Asp Leu Pro Phe Cys Lys
             20                  25                  30

Gly Asp Val Leu Thr Ile Val Ala Val Thr Lys Asp Pro Asn Trp Tyr
             35                  40                  45

Lys Ala Lys Asn Lys Val Gly Arg Glu Gly Ile Ile Pro Ala Asn Tyr
 50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
                 85                  90                  95

Tyr Pro Pro Glu Thr Gly Leu Phe Leu Val Arg Glu Ser Thr Asn Tyr
                100                 105                 110

Pro Gly Asp Tyr Thr Leu Cys Val Ser Cys Asp Gly Lys Val Glu His
                115                 120                 125

Tyr Arg Ile Met Tyr His Ala Ser Lys Leu Ser Ile Asp Glu Glu Val
            130                 135                 140

Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
                180                 185                 190

Lys Glu Leu Lys Leu Leu Gln Thr Ile Gly Lys Gly Glu Phe Gly Asp
            195                 200                 205

Val Met Leu Gly Asp Tyr Arg Gly Asn Lys Val Ala Val Lys Cys Ile
210                 215                 220

Lys Asn Asp Ala Thr Ala Gln Ala Phe Leu Ala Glu Ala Ser Val Met
225                 230                 235                 240

Thr Gln Leu Arg His Ser Asn Leu Val Gln Leu Leu Gly Val Ile Val
                245                 250                 255

Glu Glu Lys Gly Gly Leu Tyr Ile Val Thr Glu Tyr Met Ala Lys Gly
                260                 265                 270

Ser Leu Val Asp Tyr Leu Arg Ser Arg Gly Arg Ser Val Leu Gly Gly
            275                 280                 285

Asp Cys Leu Leu Lys Phe Ser Leu Asp Val Cys Glu Ala Met Glu Tyr
            290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Ser Thr Gln Asp Thr Gly Lys Leu Pro Val Lys Trp
            340                 345                 350

Thr Ala Pro Glu Ala Leu Arg Glu Lys Lys Phe Ser Thr Lys Ser Asp
            355                 360                 365

Val Trp Ser Phe Gly Ile Leu Leu Trp Glu Ile Tyr Ser Phe Gly Arg
            370                 375                 380

Val Pro Tyr Pro Arg Ile Pro Leu Lys Asp Val Val Pro Arg Val Glu
385                 390                 395                 400

Lys Gly Tyr Lys Met Asp Ala Pro Asp Gly Cys Pro Pro Ala Val Tyr
                405                 410                 415

Glu Val Met Lys Asn Cys Trp His Leu Asp Ala Ala Met Arg Pro Ser
```

```
                    420                 425                 430
Phe Leu Gln Leu Arg Glu Gln Leu Glu His Ile Lys Thr His Glu Leu
        435                 440                 445
His Leu
    450

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence:9E10-myc
      epitope tag

<400> SEQUENCE: 6

Val Asp Met Glu Gln Lys Leu Ile Ala Glu Glu Asp Leu Asn
 1               5                  10
```

METHODS AND COMPOSITIONS USEFUL FOR MODULATION OF ANGIOGENESIS USING TYROSINE KINASE SRC

CROSS-REFERENCE TO RELATED APPLICATIONS

This application is a division of U.S. patent application Ser. No. 09/701,500, filed Nov. 29, 2000, now abandoned, which is a U.S. National Stage of PCT/US99/11780, filed May 28, 1999, which claims benefit of U.S. Provisional Patent Application Ser. No. 60/087,220 filed May 29, 1998.

GOVERNMENTAL RIGHTS

This invention was made with government support under Contract No. HL 09435 by the National Institutes of Health. The government has certain rights in this invention.

TECHNICAL FIELD

The present invention relates generally to the field of medicine, and relates specifically to methods and compositions for modulating angiogenesis of tissues using the protein tyrosine kinase Src, variants of Src, and nucleic acids encoding them.

BACKGROUND

Angiogenesis is a process of tissue vascularization that involves the growth of new developing blood vessels into a tissue, and is also referred to as neo-vascularization. The process is mediated by the infiltration of endothelial cells and smooth muscle cells. The process is believed to proceed in any one of three ways: the vessels can sprout from pre-existing vessels, de-novo development of vessels can arise from precursor cells (vasculogenesis), or existing small vessels can enlarge in diameter. Blood et al., *Bioch. Biophys. Acta*, 1032:89-118 (1990).

Angiogenesis is an important process in neonatal growth, but is also important in wound healing and in the pathogenesis of a large variety of clinical diseases including tissue inflammation, arthritis, tumor growth, diabetic retinopathy, macular degeneration by neovascularization of the retina and like conditions. These clinical manifestations associated with angiogenesis are referred to as angiogenic diseases. Folkman et al., *Science*, 235:442-447 (1987). Angiogenesis is generally absent in adult or mature tissues, although it does occur in wound healing and in the corpus luteum growth cycle. See, for example, Moses et al., *Science*, 248:1408-1410 (1990).

It has been proposed that inhibition of angiogenesis would be a useful therapy for restricting tumor growth. Inhibition of angiogenesis has been proposed by (1) inhibition of release of "angiogenic molecules" such as bFGF (basic fibroblast growth factor), (2) neutralization of angiogenic molecules, such as by use of anti-βbFGF antibodies, (3) use of inhibitors of vitronectin receptor $\alpha_v\beta_3$, and (4) inhibition of endothelial cell response to angiogenic stimuli. This latter strategy has received attention, and Folkman et al., *Cancer Biology*, 3:89-96 (1992), have described several endothelial cell response inhibitors, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like that might be used to inhibit angiogenesis. For additional proposed inhibitors of angiogenesis, see Blood et al., *Bioch. Biophys. Acta.*, 1032:89-118 (1990), Moses et al., *Science*, 248:1408-1410 (1990), Ingber et al., *Lab. Invest.*, 59:44-51 (1988), and U.S. Pat. Nos. 5,092,885, 5,112,946, 5,192,744, 5,202,352, 5,753,230 and 5,766,591. None of the inhibitors of angiogenesis described in the foregoing references involve the Src proteins.

For angiogenesis to occur, endothelial cells must first degrade and cross the blood vessel basement membrane in a similar manner used by tumor cells during invasion and metastasis formation.

It has been previously reported that angiogenesis depends on the interaction between vascular integrins and extracellular matrix proteins. Brooks et al., *Science*, 264:569-571 (1994). Furthermore, it was reported that programmed cell death (apoptosis) of angiogenic vascular cells is initiated by the interaction, which would be inhibited by certain antagonists of the vascular integrin $\alpha_v\beta_3$. Brooks et al., *Cell*, 79:1157-1164 (1994). More recently, it has been reported that the binding of matrix metalloproteinase-2 (MMP-2) to vitronectin receptor ($\alpha_v\beta_5$) can be inhibited using $\alpha_v\beta_5$ antagonists, and thereby inhibit the enzymatic function of the proteinase. Brooks et al., *Cell*, 85:683-693 (1996).

SUMMARY OF THE INVENTION

The present invention is directed to modulation of angiogenesis in tissues by tyrosine kinase Src, also referred to generically herein as Src.

Compositions and methods for modulating angiogenesis in a tissue associated with a disease condition are contemplated. A composition comprising an angiogenesis-modulating amount of a Src protein is administered to tissue to be treated for a disease condition that responds to modulation of angiogenesis. The composition providing the Src protein can contain purified protein, biologically active protein fragments, recombinantly produced Src protein or protein fragments or fusion proteins thereof, or gene/nucleic acid expression vectors for expressing a Src protein.

Where the Src protein is inactivated or inhibited, the modulation is an inhibition of angiogenesis. Where the Src protein is active or activated, the modulation is a potentiation of angiogenesis.

The tissue to be treated can be any tissue in which modulation of angiogenesis is desirable. For angiogenesis inhibition, it is useful to treat diseased tissue where deleterious neovascularization is occurring. Exemplary tissues include inflamed tissue, solid tumors, metastases, tissues undergoing restenosis, and the like tissues.

For potentiation, it is useful to treat patients with ischemic limbs in which there is poor circulation in the limbs from diabetic or other conditions. Patients with chronic wounds that do not heal and therefore could benefit from the increase in vascular cell proliferation and neovascularization can be treated as well.

Particularly preferred is the use of Src protein containing a modified amino acid sequence as described herein. Several particularly useful modified Src proteins and the expression thereof are described herein.

The present invention also encompasses a pharmaceutical composition for stimulating angiogenesis in a target mammalian tissue comprising a viral or non-viral gene transfer vector containing a nucleic acid and a pharmaceutically acceptable carrier or excipient; said nucleic acid having a nucleic acid segment encoding for a src protein, said src protein having any amino acid residue at codon 527 except tyrosine, serine or threonine.

Also envisioned is a pharmaceutical composition for inhibiting angiogenesis in a target mammalian tissue comprising a viral or non-viral gene transfer vector containing a nucleic acid and a pharmaceutically acceptable carrier or excipient; said nucleic acid having a nucleic acid segment encoding for a src protein having no kinase activity.

BRIEF DESCRIPTION OF THE DRAWINGS

In the drawings forming a portion of this disclosure:

FIG. 1 is a cDNA sequence of chicken c-Src which is the complete coding sequence with the introns deleted as first described by Takeya et al., *Cell*, 32:881-890 (1983). The sequence is accessible through GenBank Accession Number J00844. The sequence contains 1759 nucleotides with the protein coding portion beginning and ending at the respective nucleotide positions 112 and 1713.

FIG. 2 is the encoded amino acid residue sequence of chicken c-Src of the coding sequence shown in FIG. 1.

FIG. 3 is a cDNA sequence of human c-Src which as first described by Braeuninger et al., *Proc. Natl. Acad. Sci., USA*, 88:10411-10415 (1991). The sequence is accessible through GenBank Accession Number X59932 X71157. The sequence contains 2187 nucleotides with the protein coding portion beginning and ending at the respective nucleotide positions 134 and 1486.

FIG. 4 is the encoded amino acid residue sequence of human c-Src of the coding sequence shown in FIG. 3.

FIG. 6 illustrates the effect of retrovirus-mediated gene expression of c-Src A on angiogenesis in the chick chorioallantoic membrane (CAM) as described in Example 4. Nine-day-old chick CAMs were exposed to RCAS-Src A (active mutated c-Src) or control RCAS-GFP (Green Fluorescent Protein; a fluorescent indicator protein) retroviruses or buffer for 72 h. The level of angiogenesis was quantified as shown in FIG. 6A with representative photomicrographs (4×) in FIG. 6B corresponding to each treatment taken with a stereomicroscope.

FIG. 7 illustrates the retroviral expression of c-Src A in activating vascular MAP kinase phosphorylation.

FIG. 9 illustrates the results of retroviral delivery of RCAS-Src 251 to human tumors.

DETAILED DESCRIPTION OF THE INVENTION

A. Definitions

Figure 5:
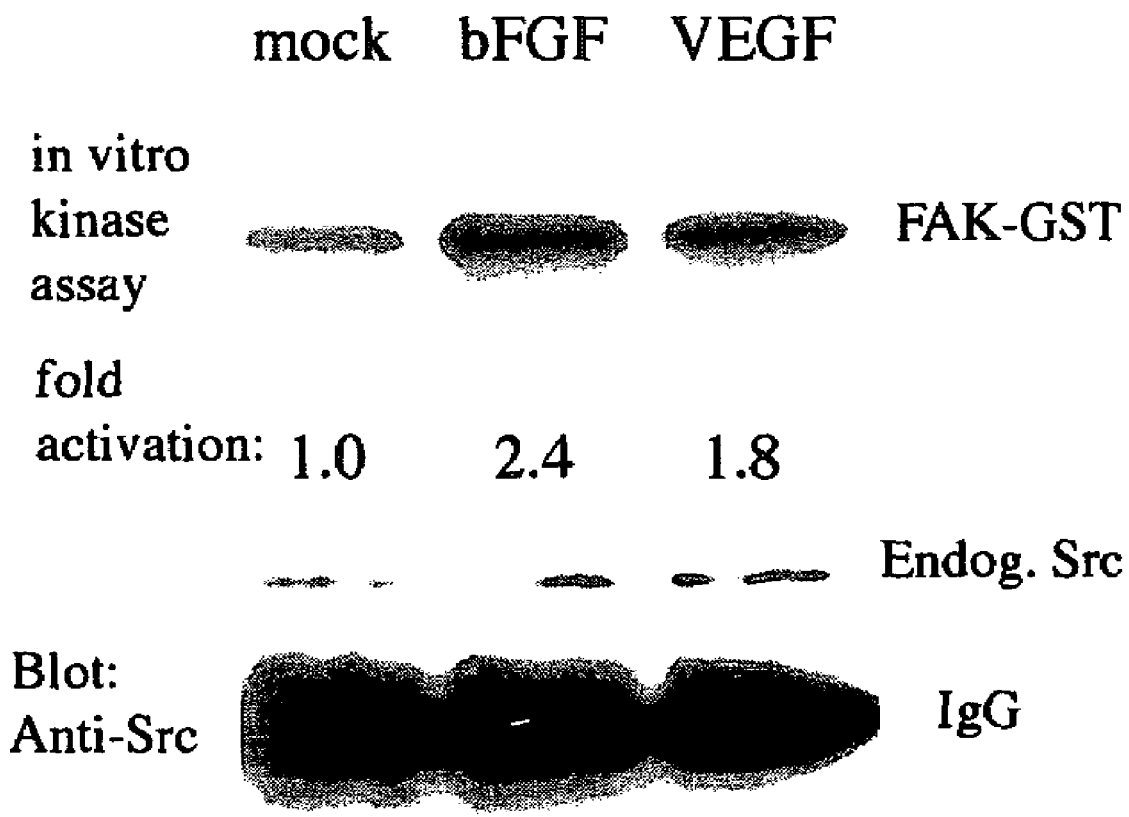
FIG. 5 illustrates the activation of endogenous Src by bFGF or VEGF as described in Example 4. The top portion of the figure indicates the results of an in vitro kinase assay with the fold activation of endogenous c-Src by either bFGF and VEGF. The bottom portion of the figure is the kinase assay blot probed with an anti-Src antibody as a loading control for equivalent Src and IgG content.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide in keeping with standard polypeptide nomenclature (described in *J. Biol. Chem.*, 243:3552-59 (1969) and adopted at 37 CFR §1.822(b)(2)).

It should be noted that all amino acid residue sequences are represented herein by formulae whose left and right orientation is in the conventional direction of amino-terminus to carboxy-terminus. Furthermore, a dash at the beginning or end of an amino acid residue sequence indicates a peptide bond to a further sequence of one or more amino acid residues.

Polypeptide: refers to a linear array of amino acid residues connected to one another by peptide bonds between the alpha-amino group and carboxy group of contiguous amino acid residues.

Peptide: as used herein refers to a linear array of no more than about 50 amino acid residues connected one to the other as in a polypeptide.

Cyclic peptide: refers to a compound having a ring structure that includes several amide bonds as in a typical peptide. The cyclic peptide can be a "head to tail" homodetic cyclic peptide, or it can contain a heterodetic ring structure in which the ring is closed by disulfide bridges, lactam bridges, thioesters, thioamides, guanidino, and the like linkages.

Protein: refers to a linear array of more than 50 amino acid residues connected one to the other as in a polypeptide.

Fusion protein: refers to a polypeptide containing at least two different polypeptide domains operatively linked by a typical peptide bond ("fused"), where the two domains correspond to peptides no found fused in nature.

Synthetic peptide: refers to a chemically produced chain of amino acid residues linked together by peptide bonds that is free of naturally occurring proteins and fragments thereof.

B. General Considerations

The present invention relates generally to the discovery that angiogenesis is mediated by the tyrosine kinase Src protein, and that angiogenesis can be modulated by providing either active or inactive Src proteins for potentiating or inhibiting angiogenesis, respectively.

This discovery is important because of the role that angiogenesis, the formation of new blood vessels, plays in a variety of disease processes. Where tissues associated with a disease condition require angiogenesis for tissue growth, it is desirable to inhibit angiogenesis and thereby inhibit the diseased tissue growth. Where injured tissue requires angiogenesis for tissue growth and healing, it is desirable to potentiate or promote angiogenesis and thereby promote tissue healing and growth.

Where the growth of new blood vessels is the cause of, or contributes to, the pathology associated with a diseased tissue, inhibition of angiogenesis reduces the deleterious effects of the disease. By inhibiting angiogenesis, one can intervene in the disease, ameliorate the symptoms, and in some cases cure the disease.

Examples of tissue associated with disease and neovascularization that will benefit from inhibitory modulation of angiogenesis include rheumatoid arthritis, diabetic retinopathy, inflammatory diseases, restenosis, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

Where the growth of new blood vessels contributes to healing of tissue, potentiation of angiogenesis assists in healing. Examples include treatment of patients with ischemic limbs in which there is poor circulation in the limbs from diabetes or other conditions. Also contemplated for treatment are patients with chronic wounds that do not heal and therefore could benefit from the increase in vascular cell proliferation and neovascularization.

The methods of the present invention are effective in part because the therapy is highly selective for angiogenesis and not other biological processes.

As described earlier, angiogenesis includes a variety of processes involving neovascularization of a tissue including "sprouting", vasculogenesis, or vessel enlargement, all of which angiogenesis processes are effected by Src protein. With the exception of traumatic wound healing, corpus luteum formation and embryogenesis, it is believed that the majority of angiogenesis processes are associated with disease processes. Accordingly, the present therapeutic methods are selective for the disease and do not have deleterious side effects.

C. Src Proteins

A tyrosine kinase Src protein for use in the present invention can vary depending upon the intended use. The terms "Src protein" or "Src" are used to refer to the various forms of tyrosine kinase Src proteins described herein, either in active or inactive forms.

An "active Src protein" refers to any of a variety of forms of src protein which potentiate angiogenesis. Assays to measure potentiation of angiogenesis are described herein, and are not to be construed as limiting. A protein is considered active if the level of angiogenesis is at least 10% greater, preferably 25% greater, and more preferably 50% greater than a control level where no src is added to the assay system. The preferred assay for measuring potentiation is the CAM assay using RCAS viral vector as described in the Examples in which the angiogenic index is calculated by counting branch points. A preferred active Src protein exhibits tyrosine kinase activity as well. Exemplary active Src proteins are described in the Examples, and include Src-A.

An "inactive Src protein" refers to any of a variety of forms of Src protein which inhibit angiogenesis. Assays to measure inhibition of angiogenesis are described herein, and are not to be construed as limiting. A protein is considered inactive if the level of angiogenesis is at least 10% lower, preferably 25% lower, and more preferably 50% lower than a control level where no exogenous Src is added to the assay system. The preferred assay for measuring inhibition is the CAM assay using RCAS viral vector as described in the Examples in which the angiogenic index is calculated by counting branch points. A preferred inactive Src protein exhibits reduced tyrosine kinase activity as well. Exemplary inactive Src proteins are described in the Examples, and include Src-251.

A Src protein useful in the present invention can be produced in any of a variety of methods including isolation from natural sources including tissue, production by recombinant DNA expression and purification, and the like. Src protein can also be provided "in situ" by introduction of a gene therapy system to the tissue of interest which then expresses the protein in the tissue.

A gene encoding a Src protein can be prepared by a variety of methods known in the art, and the invention is not to be construed as limiting in this regard. For example, the natural history of Src is well known to include a variety of homologs from mammalian, avian, viral and the like species, and the gene can readily be cloned using cDNA cloning methods from any tissue expressing the protein. A preferred Src for use in the invention is a cellular protein, such as the mammalian or avian homologs designated c-Src. Particularly preferred is human c-Src.

D. Recombinant DNA Molecules and Expression Systems for Expression of a Src Protein The invention describes several nucleotide sequences of particular use in the present invention. These sequences include sequences which encode a Src protein useful in the invention, and various DNA segments, recombinant DNA (rDNA) molecules and vectors constructed for expression of Src protein.

DNA molecules (segments) of this invention therefore can comprise sequences which encode whole structural genes, fragments of structural genes, and transcription units as described further herein.

A preferred DNA segment is a nucleotide sequence which encodes a Src protein as defined herein, or biologically active fragment thereof, The amino acid residue sequence and nucleotide sequence of a preferred c-Src is described in the Examples.

A preferred DNA segment codes for an amino acid residue sequence substantially the same as, and preferably consisting essentially of, an amino acid residue sequence or portions thereof corresponding to a Src protein described herein. Representative and preferred DNA segments are further described in the Examples.

The amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A nucleic acid is any polynucleotide or nucleic acid fragment, whether it be a polyribonucleotide of polydeoxyribonucleotide, i.e., RNA or DNA, or analogs thereof. In preferred embodiments, a nucleic acid molecule is in the form of a segment of duplex DNA, i.e, a DNA segment, although for certain molecular biological methodologies, single-stranded DNA or RNA is preferred.

DNA segments are produced by a number of means including chemical synthesis methods and recombinant approaches, preferably by cloning or by polymerase chain reaction (PCR). DNA segments that encode portions of a Src protein can easily be synthesized by chemical techniques, for example, the phosphotriester method of Matteucci et al, *J. Am. Chem. Soc.*, 103:3185-3191, 1981, or using automated synthesis methods. In addition, larger DNA segments can readily be prepared by well known methods, such as synthesis of a group of oligonucleotides that define the DNA segment, followed by hybridization and ligation of oligonucleotides to build the complete segment. Alternative methods include isolation of a preferred DNA segment by PCR with a pair of oligonucleotide primers used on a cDNA library believed to contain members which encode a Src protein.

Of course, through chemical synthesis, any desired modifications can be made simply by substituting the appropriate bases for those encoding the native amino acid residue sequence. This method is well known, and can be readily applied to the production of the various different "modified" Src proteins described herein.

Furthermore, DNA segments consisting essentially of structural genes encoding a Src protein can be subsequently modified, as by site-directed or random mutagenesis, to introduce any desired substitutions.

1. Cloning a Src Gene

A Src gene can be cloned from a suitable source of genomic DNA or messenger RNA (mRNA) by a variety of biochemical methods. Cloning of these genes can be conducted according to the general methods described in the Examples and as known in the art.

Sources of nucleic acids for cloning a Src gene suitable for use in the methods of this invention can include genomic DNA or messenger RNA (mRNA) in the form of a cDNA library, from a tissue believed to express these proteins. A preferred tissue is human lung tissue, although any other suitable tissue may be used.

A preferred cloning method involves the preparation of a cDNA library using standard methods, and isolating the Src-encoding nucleotide sequence by PCR amplification using paired oligonucleotide primers based on the nucleotide sequences described herein. Alternatively, the desired cDNA clones can be identified and isolated from a cDNA or genomic library by conventional nucleic acid hybridization methods using a hybridization probe based on the nucleic acid sequences described herein. Other methods of isolating and cloning suitable src encoding nucleic acids are readily apparent to one skilled in the art.

2. Expression Vectors

A recombinant DNA molecule (rDNA) containing a DNA segment encoding a Src protein can be produced as described herein. In particular, an expressible rDNA can be produced by operatively (in frame, expressibly) linking a vector to a src encoding DNA segment. Thus, a recombinant DNA molecule is a hybrid DNA molecule comprising at least two nucleic acids of a nucleotide sequences not normally found together in nature.

The choice of vector to which the DNA segment is operatively linked depends directly, as is well known in the art, on the functional properties desired, e.g., protein expression, and the host cell to be transformed. A vector suitable for use in practicing the present invention is at least capable of directing the replication, and preferably also expression, of a structural gene included in the vector DNA segments to which it is operatively linked.

Both prokaryotic and eukaryotic expression vectors are familiar to one of ordinary skill in the art of vector construction, and are described by Ausebel, et al., in *Current Protocols in Molecular Biology*, Wiley and Sons, New York (1993) and by Sambrook et al., *Molecular Cloning: A Laboratory Manual*, Cold Spring Harbor Laboratory, (1989). These references also describe many of the general recombinant DNA methods referred to herein.

In one embodiment, a suitable vector includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a structural gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pRSET available from Invitrogen (San Diego, Calif.) and pPL and pKK223 available from Pharmacia, Piscataway, N.J.

Expression vectors compatible with eukaryotic cells, preferably those compatible with vertebrate cells, can also be used to form the recombinant DNA molecules of the present invention. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), pRc/CMV (Invitrogen, Inc.), the preferred vector described in the Examples, and the like eukaryotic expression vectors.

A particularly preferred system for gene expression in the context of this invention includes a gene delivery component, that is, the ability to deliver the gene to the tissue of interest. Suitable vectors are "infectious" vectors such as recombinant DNA viruses, adenovirus or retrovirus vectors which are engineered to express the desired protein and have features which allow infection of preselected target tissues. Particularly preferred is the replication competent avian sarcoma virus (RCAS) described herein.

Mammalian cell systems that utilize recombinant viruses or viral elements to direct expression may be engineered. For example, when using adenovirus expression vectors, the coding sequence of a polypeptide may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the polypeptide in infected hosts (e.g., see Logan et al., *Proc. Natl. Acad. Sci. USA*, 81:3655-3659 (1984)). Alternatively, the vaccinia virus 7.5K promoter may be used (e.g., see, Mackett et al., *Proc. Natl. Acad. Sci. USA*, 79:7415-7419 (1982); Mackett et al., *J. Virol.*, 49:857-864 (1984); Panicali et al., *Proc. Natl. Acad. Sci., USA*, 79:4927-4931 (1982)). Of particular interest are vectors based on bovine papilloma virus which have the ability to replicate as extrachromosomal elements (Sarver et al., *Mol. Cell. Biol.*, 1:486 (1981)). Shortly after entry of this DNA into target cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the polypeptide-encoding nucleotide sequence in host cells (Cone et al., *Proc. Natl. Acad. Sci., USA*, 81:6349-6353 (1984)). High level expression may also be achieved using inducible promoters, including, but not limited to, the metallothionine IIA promoter and heat shock promoters.

Recently, long-term survival of cytomegalovirus (CMV) promoter versus Rous sarcoma virus (RSV) promotor-driven thymidine kinase (TK) gene therapy in nude mice bearing human ovarian cancer has been studied. Cell killing efficacy of adenovirus-mediated CMV promoter-driven herpes simplex virus TK gene therapy was found to be 2 to 10 time more effective than RSV driven therapy. (Tong et al., 1999, *Hybridoma* 18(1):93-97). The design of chimeric promoters for gene therapy applications, which call for low level expression followed by inducible high-level expression has also been described. (Suzuki et al., 1996, *Human Gene Therapy* 7:1883-1893).

For long-term, high-yield production of recombinant proteins, stable expression is preferred. Rather than using expression vectors which contain viral origins of replication, host cells can be transformed with a cDNA controlled by appropriate expression control elements (e.g., promoter and enhancer sequences, transcription terminators, polyadenylation sites, etc.), and a selectable marker. As mentioned above, the selectable marker in the recombinant plasmid confers resistance to the selection and allows cells to stably integrate the plasmid into their chromosomes and grow to form foci which in turn can be cloned and expanded into cell lines.

For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler et al., *Cell*, 11:223 (1977)), hypoxanthine-guanine phosphoribosyltransferase (Szybalska et al, *Proc. Natl. Acad. Sci., USA*, 48:2026 (1962)), and adenine phosphoribosyltransferase (Lowy et al., *Cell*, 22:817 (1980)) genes, which can be employed in $tk^-$, $hgprt^-$ or $aprt^-$ cells respectively. Also, antimetabolite resistance-conferring genes can be used as the basis of selection; for example, the genes for dhfr, which confers resistance to methotrexate (Wigler et al., *Proc. Natl. Acad. Sci., USA*, 77:3567 (1980); O'Hare et al., *Proc. Natl. Acad. Sci., USA*, 78:1527 (1981); gpt, which confers resistance to mycophenolic acid (Mulligan et al, *Proc. Natl. Acad. Sci., USA*, 78:2072, (1981)); neo, which confers resistance to the aminoglycoside G-418 (Colberre-Garapin et al, *J. Mol. Biol.*, 150:1 (1981)); and hygro, which confers resistance to hygromycin (Santerre et al, *Gene*, 30:147 (1984)). Recently, additional selectable genes have been described, namely trpB, which allows cells to utilize indole in place of tryptophan; hisD, which allows cells to utilize histinol in place of histidine (Hartman et al, *Proc. Natl. Acad. Sci., USA*, 85:804 (1988)); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., (1987)).

The principal vectors contemplated for human gene therapy are derived from retroviral origin. (Wilson, 1997, *Clin. Exp. Immunol.* 107(Sup. 1):31-32; Bank et al., 1996, *Bioessays* 18(12):999-1007; Robbins et al., 1998, *Pharmacol. Ther.* 80(1):35-47). The therapeutic potential of gene transfer and antisense therapy has stimulated the development of many vector systems for treating a variety of tissues. (vasculature, Stephan et al., 1997, *Fundam. Clin. Pharmacol.* 11(2):97-110; Feldman et al., 1997, *Cardiovasc. Res.* 35(3):391-404; Vassalli et al., 1997, *Cardiovasc. Res.* 35(3):459-69; Baek et al., 1998, *Circ. Res.* 82(3):295-305; kidney, Lien et al., 1997, *Kidney Int. Suppl.* 61:S85-8; liver, Ferry et al., 1998, *Hum Gene Ther.* 9(14):1975-81; muscle, Marshall et al., 1998, *Curr. Opn. Genet. Dev.* 8(3):360-5). In addition to these tissues, a critical target for human gene therapy is cancer, either the tumor itself, or associated tissues. (Runnebaum, 1997, *Anticancer Res.* 17(4B):2887-90; Spear et al., 1998, *J. Neurovirol.* 4(2): 133-47).

Specific examples of viral gene therapy vector systems readily adaptable for use in the methods of the present invention are briefly described below. Retroviral gene delivery has been recently reviewed by Federspiel and Hughes (1998, *Methods in Cell Biol.* 52:179-214) which describes in particular, the avian leukosis virus (ALV) retrovirus family (Federspiel et al., *Proc. Natl. Acad. Sci., USA*, 93:4931 (1996); Federspiel et al., *Proc. Natl. Acad. Sci., USA*, 91:11241 (1994)). Retroviral vectors, including ALV and murine leukemia virus (MLV) are further described by Svoboda (1998, *Gene* 206:153-163).

Modified retroviral/adenoviral expression systems can be readily adapted for practice of the methods of the present invention. For example, murine leukemia virus (MLV) systems are reviewed by Karavanas et al., 1998, *Crit. Rev. in Oncology/Hematology* 28:7-30. Adenovirus expression systems are reviewed by Von Seggern and Nemerow in *Gene Expression Systems* (ed. Fernandez & Hoeffler, Academic Press, San Diego, Calif., 1999, chapter 5, pages 112-157).

Protein expression systems have been demonstrated to have effective use both in vivo and in vitro. For example, efficient gene transfer to human squamous cell carcinomas by a herpes simplex virus (HSV) type 1 amplicon vector has been described. (Carew et al., 1998, *Am. J. Surg.* 176:404-408). Herpes simplex virus has been used for gene transfer to the nervous system. (Goins et al., 1997, *J. Neurovirol.* 3 (Sup. 1):S80-8). Targeted suicide vectors using HSV-TK has been tested on solid tumors. (Smiley et al., 1997, *Hum. Gene Ther.* 8(8):965-77). Herpes simplex virus type 1 vector has been used for cancer gene therapy on colon carcinoma cells. (Yoon et al., 1998, *Ann. Surg.* 228(3):366-74). Hybrid vectors have been developed to extend the length of time of transfection, including HSV/AAV (adeno-associated virus) hybrids for treating hepatocytes. (Fraefel et al., 1997, *Mol. Med.* 3(12): 813-825).

Vaccinia virus has been developed for human gene therapy because of its large genome. (Peplinski et al., 1998, *Surg. Oncol. Clin. N. Am.* 7(3):575-88). Thymidine kinase-deleted vaccinia virus expressing purine nucleoside pyrophosphorylase has been described for use as a tumor directed gene therapy vector. (Puhlman et al., 1999, *Human Gene Therapy* 10:649-657).

Adeno-associated virus 2 (AAV) has been described for use in human gene therapy, however AAV requires a helper virus (such as adenovirus or herpes virus) for optimal replication and packaging in mammalian cells. (Snoeck et al., 1997, *Exp. Nephrol.* 5(6):514-20; Rabinowitz et al., 1998, *Curr. Opn. Biotechnol.* 9(5):470-5). However, in vitro packaging of an infectious recombinant AAV has been described, making this system much more promising. (Ding et al., 1997, *Gene Therapy* 4:1167-1172). It has been shown that the AAV mediated transfer of ecotropic retrovirus receptor cDNA allows ecotropic retroviral transduction of established and primary human cells. (Qing et al., 1997, *J. Virology* 71(7): 5663-5667). Cancer gene therapy using an AAV vector expressing human wild-type p53 has been demonstrated. (Qazilbash et al., 1997, *Gene Therapy* 4:675-682). Gene transfer into vascular cells using AAV vectors has also been shown. (Maeda et al., 1997, *Cardiovascular Res.* 35:514-521). AAV has been demonstrated as a suitable vector for liver directed gene therapy. (Xiao et al., 1998, *J. Virol.* 72(12): 10222-6). AAV vectors have been demonstrated for use in gene therapy of brain tissues and the central nervous system. (Chamberlin et al., 1998, *Brain Res.* 793(1-2):169-75; During et al., 1998, *Gene Therapy* 5(6):820-7). AAV vectors have also been compared with adenovirus vectors (AdV) for gene therapy of the lung and transfer to human cystic fibrosis epithelial cells. (Teramoto et al., 1998, *J. Virol.* 72(11):8904-12).

Chimeric AdV/retroviral gene therapy vector systems which incorporate the useful qualities of each virus to create a nonintegrative AdV that is rendered functionally integrative via the intermediate generation of a retroviral producer cell. (Feng et al., 1997, *Nat. Biotechnology* 15(9):866-70; Bilbao et al., 1997, *FASEB J* 11(8):624-34). This powerful new generation of gene therapy vector has been adapted for targeted cancer gene therapy. (Bilbao et al., 1998, *Adv. Exp. Med. Biol.* 451:365-74). Single injection of AdV expressing p53 inhibited growth of subcutaneous tumor nodules of human prostrate cancer cells. (Asgari et al., 1997, *Int. J. Cancer* 71(3): 377-82). AdV mediated gene transfer of wild-type p53 in patients with advanced non-small cell lung cancer has been described. (Schuler et al., 1998, *Human Gene Therapy* 9:2075-2082). This same cancer has been the subject of p53 gene replacement therapy mediated by AdV vectors. (Roth et al., 1998, *Semin. Oncol.* 25(3 Suppl 8):33-7). AdV mediated gene transfer of p53 inhibits endothelial cell differentiation and angiogenesis in vivo. (Riccioni et al., 1998, *Gene Ther.* 5(6):747-54). Adenovirus-mediated expression of melanoma antigen gp75 as immunotherapy for metastatic melanoma has also been described. (Hirschowitz et al., 1998, *Gene Therapy* 5:975-983). AdV facilitates infection of human cells with ecotropic retrovirus and increases efficiency of retroviral infection. (Scott-Taylor, et al., 1998, *Gene Ther.* 5(5):621-9). AdV vectors have been used for gene transfer to vascular smooth muscle cells (Li et al., 1997, *Chin. Med. J. (Engl)* 110(12):950-4), squamous cell carcinoma cells (Goebel et al., 1998, *Otolarynol Head Neck Surg* 119(4):331-6), esophageal cancer cells (Senmaru et al., 1998, *Int J. Cancer* 78(3): 366-71), mesangial cells (Nahman et al., 1998, *J. Investig. Med.* 46(5):204-9), glial cells (Chen et al., 1998, *Cancer Res.* 58(16):3504-7), and to the joints of animals (Ikeda et al., 1998, *J. Rheumatol.* 25(9):1666-73). More recently, catheter-based pericardial gene transfer mediated by AcV vectors has been demonstrated. (March et al., 1999, *Clin. Cardiol.* 22(1 Suppl 1):I23-9). Manipulation of the AdV system with the proper controlling genetic elements allows for the AdV-mediated regulable target gene expression in vivo. (Burcin et al., 1999, *PNAS (USA)* 96(2):355-60).

Alphavirus vectors have been developed for human gene therapy applications, with packaging cell lines suitable for transformation with expression cassettes suitable for use with Sindbis virus and Semliki Forest virus-derived vectors. (Polo et al., 1999, *Proc. Natl. Acad. Sci., USA.* 96:4598-4603). Noncytopathic flavivirus replicon RNA-based systems have also been developed. (Varnavski et al., 1999, *Virology* 255(2): 366-75). Suicide HSV-TK gene containing sinbis virus vectors have been used for cell-specific targeting into tumor cells. (Iijima et al., 1998, *Int. J. Cancer* 80(1): 110-8).

Retroviral vectors based on human foamy virus (HFV) also show promise as gene therapy vectors. (Trobridge et al., 1998, *Human Gene Therapy* 9:2517-2525). Foamy virus vectors have been designed for suicide gene therapy. (Nestler et al., 1997, *Gene Ther.* 4(11): 1270-7). Recombinant murine cytomegalovirus and promoter systems have also been used as vectors for high level expression. (Manning et al., 1998, *J. Virol. Meth.* 73(1):31-9; Tong et al., 1998, *Hybridoma* 18(1): 93-7).

Gene delivery into non-dividing cells has been made feasible by the generation of Sendai virus based vectors. (Nakanishi et al., 1998, *J. Controlled Release* 54(1):61-8).

In other efforts to enable the transformation of non-dividing somatic cells, lentiviral vectors have been explored. Gene therapy of cystic fibrosis using a replication-defective human immunodeficiency virus (HIV) based vector has been described. (Goldman et al., 1997, *Human Gene Therapy* 8:2261-2268). Sustained expression of genes delivered into liver and muscle by lentiviral vectors has also been shown. (Kafri et al., 1997, *Nat. Genet.* 17(3):314-7). However, safety concerns are predominant, and improved vector development is proceeding rapidly. (Kim et al., 1998, *J. Virol.* 72(2):994-1004). Examination of the HIV LTR and Tat yield important information about the organization of the genome for developing vectors. (Sadaie et al., 1998, *J. Med. Virol.* 54(2):118-28). Thus the genetic requirements for an effective HIV based vector are now better understood. (Gasmi et al., 1999, *J. Virol.* 73(3): 1828-34). Self inactivating vectors, or conditional packaging cell lines have been described. (for example Zuffery et al., 1998, *J. Virol.* 72(12):9873-80; Miyoshi et al., 1998, *J. Virol.* 72(10):8150-7; Dull et al., 1998, *J. Virol.* 72(11):8463-71; and Kaul et al., 1998, *Virology* 249(1):167-74). Efficient transduction of human lymphocytes and CD34+ cells by HIV vectors has been shown. (Douglas et al., 1999, *Hum. Gene Ther.* 10(6):935-45; Miyoshi et al., 1999, *Science* 283(5402):682-6). Efficient transduction of nondividing human cells by feline immunodeficiency virus (FIV) lentiviral vectors has been described, which minimizes safety concerns with using HIV based vectors. (Poeschla et al., 1998, *Nature Medicine* 4(3):354-357). Productive infection of human blood mononuclear cells by FIV vectors has been shown. (Johnston et al., 1999, *J. Virol.* 73(3):2491-8).

While many viral vectors are difficult to handle, and capacity for inserted DNA limited, these limitations and disadvantages have been addressed. For example, in addition to simplified viral packaging cell lines, Mini-viral vectors, derived from human herpes virus, herpes simplex virus type 1 (HSV-1), and Epstein-Barr virus (EBV), have been developed to simplify manipulation of genetic material and generation of viral vectors. (Wang et al., 1996, *J. Virology* 70(12):8422-8430). Adaptor plasmids have been previously shown to simplify insertion of foreign DNA into helper-independent Retroviral vectors. (1987, *J. Virology* 61(10):3004-3012).

Viral vectors are not the only means for effecting gene therapy, as several non-viral vectors have also been described. A targeted non-viral gene delivery vector based on the use of Epidermal Growth Factor/DNA polyplex (EGF/DNA) has been shown to result in efficient and specific gene delivery. (Cristiano, 1998, *Anticancer Res.* 18:3241-3246). Gene therapy of the vasculature and CNS have been demonstrated using cationic liposomes. (Yang et al., 1997, *J. Neurotrauma* 14(5):281-97). Transient gene therapy of pancreatitis has also been accomplished using cationic liposomes. (Denham et al., 1998, *Ann. Surg.* 227(6):812-20). A chitosan-based vector/DNA complexes for gene delivery have been shown to be effective. (Erbacher et al., 1998, *Pharm. Res.* 15(9):1332-9). A non-viral DNA delivery vector based on a terplex system has been described. (Kim et al., 1998, 53(1-3): 175-82). Virus particle coated liposome complexes have also been used to effect gene transfer. (Hirai et al., 1997, *Biochem. Biophys. Res. Commun.* 241(1):112-8).

Cancer gene therapy by direct tumor injections of nonviral T7 vector encoding a thymidine kinase gene has been demonstrated. (Chen et al., 1998, *Human Gene Therapy* 9:729-736). Plasmid DNA preparation is important for direct injection gene transfer. (Horn et al., 1995, *Hum. Gene Ther.* 6(5): 656-73). Modified plasmid vectors have been adapted specifically for direct injection. (Hartikka et al., 1996, *Hum. Gene Ther.* 7(10):1205-17).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked src (either active or inactive) into the selected expression/delivery vector, many equivalent vectors for the practice of the present invention can be generated.

E. Methods for Modulation of Angiogenesis

The invention provides for a method for the modulation of angiogenesis in a tissue associated with a disease process or condition, and thereby effect events in the tissue which depend upon angiogenesis. Generally, the method comprises administering to the tissue associated with a disease process or condition, a composition comprising an angiogenesis-modulating amount of a Src protein or nucleic acid vector expressing active or inactive Src.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

The patient treated according to the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of tissue associated with diseases involving angiogenesis is desirable, particularly agricultural and domestic mammalian species.

Thus the method comprises administering to a patient a therapeutically effective amount of a physiologically tolerable composition containing a Src protein or DNA vector for expressing a Src protein in practicing the methods of the invention.

The dosage ranges for the administration of a Src protein depend upon the form of the protein, and its potency, as described further herein. The dosage amounts are large enough to produce the desired effect in which angiogenesis and the disease symptoms mediated by angiogenesis are ameliorated. The dosage should not be so large as to cause adverse side effects, however, such as hyperviscosity syndromes, pulmonary edema, congestive heart failure, and the like. Generally, the dosage will vary with the age, condition, sex of the patient, and extent of the disease in the patient, and can be readily determined by one of skill in the art. The dosage can also be adjusted by the individual physician in the event of any complication.

A therapeutically effective amount is an amount of Src protein, or nucleic acid encoding for (active or inactive) src protein, sufficient to produce a detectable modulation of angiogenesis in the tissue being treated, ie., an angiogenesis-modulating amount. Modulation of angiogenesis can be measured by CAM assay as described herein, or by other methods known to one skilled in the art.

The Src protein or nucleic acid vector expressing the Src protein can be administered parenterally by injection or by gradual infusion over time. Although the tissue to be treated can typically be accessed in the body by systemic administration, and therefore is most often treated by intravenous administration of therapeutic compositions, other tissues and delivery means are contemplated as well. Thus, compositions of the invention can be administered intravenously, intraperitoneally, intramuscularly, subcutaneously, intracavity, transdermally, and can be delivered by peristaltic means.

The therapeutic compositions containing a Src protein or nucleic acid vector expressing the Src protein can be conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

In one preferred embodiment the reagent is administered in a single dosage intravenously. Localized administration can be accomplished by direct injection or by taking advantage of anatomically isolated compartments, isolating the microcirculation of target organ systems, reperfusion in a circulating system, or catheter based temporary occlusion of target regions of vasculature associated with diseased tissues.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

1. Inhibition of Angiogenesis

Inhibition of angiogenesis is important in a variety of diseases, referred to as angiogenic diseases. Such diseases include, but are not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

Thus, methods which inhibit angiogenesis in a tissue associated with a disease condition ameliorates symptoms of the disease and, depending upon the disease, can contribute to cure of the disease. In one embodiment, the invention contemplates inhibition of angiogenesis, per se, in a tissue associated with a disease condition. The extent of angiogenesis in a tissue, and therefore the extent of inhibition achieved by the present methods, can be evaluated by a variety of methods.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

In another related embodiment, a tissue to be treated is a retinal tissue of a patient with a retinal disease such as diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues. Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods can also apply to inhibition of tumor tissue growth, to inhibition of tumor metastases formation, and to regression of established tumors.

Restenosis is a process of smooth muscle cell (SMC) migration and proliferation into the tissue at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures. For inhibition of restenosis, the inactivated tyrosine kinase is typically administered after the angioplasty procedure because the coronary vessel wall is at risk of restenosis, typically for from about 2 to about 28 days, and more typically for about the first 14 days following the procedure.

The present method for inhibiting angiogenesis in a tissue associated with a disease condition, and therefore for also practicing the methods for treatment of angiogenesis-related diseases, comprises contacting a tissue in which angiogenesis is occurring, or is at risk for occurring, with a composition comprising a therapeutically effective amount of an inactivated Src protein or vector expressing the protein.

Inhibition of angiogenesis and tumor regression occurs as early as 7 days after the initial contacting with the therapeutic composition. Additional or prolonged exposure to inactive Src protein is preferable for 7 days to 6 weeks, preferably about 14 to 28 days.

2. Potentiation of Angiogenesis

In cases where it is desirable to promote or potentiate angiogenesis, administration of an active Src protein to the tissue is useful. The routes and timing of administration are comparable to the methods described hereinabove for inhibition.

F. Therapeutic Compositions

The present invention contemplates therapeutic compositions useful for practicing the therapeutic methods described herein. Therapeutic compositions of the present invention contain a physiologically tolerable carrier together with a Src protein or vector capable of expressing a Src protein as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of any salt-forming components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers for the active ingredients are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-modulating amount of an Src protein of the present invention, or sufficient recombinant DNA expression vector to express an effective amount of Src protein, typically formulated to contain an amount of at least 0.1 weight percent of Src protein per weight of total therapeutic composition. A weight percent is a ratio by weight of Src protein to total composition. Thus, for example, 0.1 weight percent is 0.1 grams of Src protein per 100 grams of total composition. For DNA expression vectors, the amount administered depends on the properties of the expression vector, the tissue to be treated, and the like considerations.

G. Article of Manufacture

The invention also contemplates an article of manufacture which is a labelled container for providing a Src protein of the invention. An article of manufacture comprises packaging material provided with appropriate labeling for the disease condition to be treated and a pharmaceutical agent contained within the packaging material.

The pharmaceutical agent in an article of manufacture is any of the compositions of the present invention suitable for providing a Src protein and formulated into a pharmaceutically acceptable form as described herein according to the disclosed indications. Thus, the composition can comprise a Src protein or a DNA molecule which is capable of expressing a Src protein. The article of manufacture contains an amount of pharmaceutical agent sufficient for use in treating a condition indicated herein, either in unit or multiple dosages.

The packaging material comprises a label which indicates the use of the pharmaceutical agent contained therein, e.g., for treating conditions assisted by the inhibition or potentiation of angiogenesis, and the like conditions disclosed herein. The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of c-Src Expression Constructs

For preparing the expression constructs useful in modulating angiogenesis by the methods of the present invention, c-Src cDNA is manipulated and inserted into an expression construct/vector.

The cDNA sequence encoding for wild-type (i.e., endogenous) chicken c-Src is shown in FIG. 1 (SEQ ID NO.:2) with the encoded amino acid residue sequence shown in FIG. 2 (SEQ ID NO.:3). The encoded protein sequence is translated from the cDNA nucleotide positions 112 to 1713. The nucleic acid sequence corresponding to the nucleic acid sequence of human c-Src cDNA (SEQ ID NO.:4) and encoded amino acid residue (SEQ ID NO.:5) sequences are shown respectively in FIGS. 3 and 4. For the human protein sequence, the coding sequence begins at nucleotide position 134 to 1486 of the cDNA.

Wild-type as well as a number of mutated c-Src cDNAs were prepared. Mutated c-Src constructs were prepared by site-directed mutagenesis as described by Kaplan et al., *EMBO J.*, 13:4745-4756 (1994). The mutated c-Src constructs for encoding mutated c-Src proteins for use in the methods of the present invention are described in Kaplan et al., id Kaplan et al. describe various mutated c-Src constructs and encoded proteins of useful for the practice of this invention. For example, Kaplan et al. depict several products of chicken c-src alleles in their FIG. 1, including SrcA and Src251.

Two categories of c-Src function to modulate angiogenesis are described. As previously discussed, one category contains Src molecules that increase angiogenesis and thus are considered to be active proteins. Wild-type Src along with various mutations are shown in the present invention to induce angiogenesis. One preferred mutation of wild type c-src which functions in this context with respect to its ability to induce blood vessel growth and therefore increase tumor weight in vivo is the Src A mutant having a point mutation at amino acid (aa) residue position 527 changing tyrosine 527 to phenylalanine. This site is normally a site for negative regulation by the c-Src kinase, referred to as kinase CSK. When CSK phosphorylates aa527 in the wild-type src, the protein is inactivated. However, in mutated Src A, the regulatory tyrosine converted to phenylalanine thus conferring upon the protein a constitutively (i.e., permanently) active protein not subject to inactivation by phosphorylation.

Mutations in src have also been shown to have the opposite modulatory effect on angiogenesis, inhibiting angiogenesis instead of stimulating it. Such mutations are referred to as inactive src mutations. Proteins having mutation that confer this inhibitory activity are also referred to as dominant negative Src proteins in that they inhibit neovascularization, including that resulting from endogenous activity of Src as well as enhanced Src activity resulting from growth factor stimulation. Thus certain mutations of wild type c-src of the present invention can also function as a dominant negative with respect to their ability to block blood vessel growth, and for example, therefore decrease tumor weight in vivo.

Such preferred inhibitory c-Src protein includes the Src 251 in which only the first 251 amino acids of Src are expressed. This construct lacks the entire kinase domain and is therefore referred to as "kinase dead" src protein. A second construct is the Src (K295M) mutation in which the lysine amino acid residue 295 is mutated into a methionine. This point mutation in the kinase domain prevents ATP binding and also blocks kinase-dependent Src functions related to vascular cell and tumor cell signaling and proliferation.

For example, for the mutation at residue 527, as long as the resultant mutated amino acid residue is not tyrosine, serine, or threonine, the present invention contemplates that the presence of an alternate amino acid at the desired position will result in a Src protein with a desired active, angiogenesis promoting modulatory activity.

With respect to the point mutations, any mutation resulting in the desired inhibitory or stimulatory activity is contemplated for use in this invention. Fusion protein constructs combining the desired src protein (mutation or fragment thereof) with expressed amino acid tags, antigenic epitopes, fluorescent protein, or other such protein or peptides are also contemplated, so long as the desired modulating effect of the src protein is intact.

TABLE I

| Src/Mutation | Src Function | Effect on Angiogenesis |
|---|---|---|
| c-Src | + active | stimulates |
| SrcA (T527F) | + active | stimulates |
| Src527 (point) | + active | stimulates |
| Src251 | − inactive | inhibits |

TABLE I-continued

| Src/Mutation | Src Function | Effect on Angiogenesis |
|---|---|---|
| Src (truncate) | − inactive | inhibits |
| Src (K295M) | − inactive | inhibits |
| Src295 (point) | − inactive | inhibits |

Figure 10:
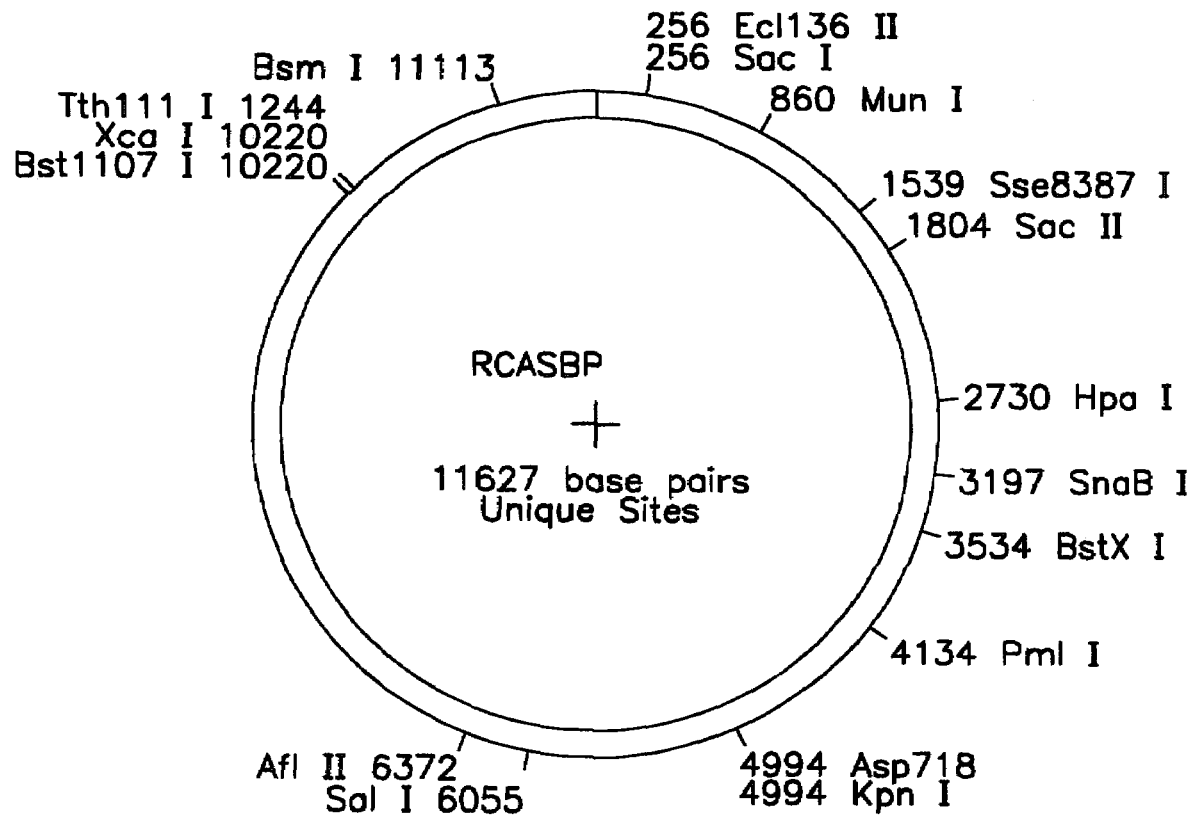
FIG. 10 is a diagram illustrating a restriction map of the RCASBP (RCAS) vector construct.

One preferred expression construct for use in the present invention is the RCASBP(A) construct (SEQ ID NO.:1). This expression vector is based on a series of replication competent avian sarcoma viruses with an enhanced Bryan polymerase (BP) for improved titre, and is specific for the A type envelope glycoprotein expressed on normal avian cells (Reviewed in Methods in Cell Biology, 52:179-214 (1997); see also, Hughes et al., 1987, *J. Virol.* 61:3004-3012; Fekete & Cepko, 1993, *Mol. Cellular Biol.* 13(4):2604-2613; Itoh et al., 1996, *Development* 122:291-300; and Stott et al., 1998, *BioTechniques* 24:660-666). The complete sequence of RCASBP(A) (SEQ ID NO.:1) is given in the attached sequence listing, and a restriction map of the construct is depicted as FIG. 10, referred to herein as RCAS.

The original Src 251 construct was subcloned by Dr. Pam Schwartzberg, at NIH in Dr. Harold Varmus' laboratory. Briefly, cloning of a src cDNA sequence for expression thereof was accomplished by inserting a linker containing Not I-BstB1-Not I restriction sites into a unique Not I site in the 5' end of Src 251. Src has a unique Cla I site at the 3' end. Digestion of Src 251 with BstB1 and Cla I generated a BstB1-ClaI fragment which was then ligated into the Cla I site on RCASBP(A). A BstB1 overhang allows for ligation with a Cla I overhang that will not be recut with Cla I. The src constructs suitable for use in practicing the present invention are readily obtained in the above vector by first digesting the RCAS vector containing Src 251 with Not I and Cla I (in a DAM+ background) to allow for insertion of a similarly digested Src cDNA. Therefore this initial RCASBP(A) construct containing Src 251 was further used to subclone all other Src constructs as described above and in Kaplan et al. (1994, *The EMBO J.* 13(20):4745-4756), into RCASBP(A) via a Not I-Cla I fragment generated through the Src 251 construction. To produce the desired c-src mutations in the cDNA, standard site-directed mutagenesis procedures familiar to one of ordinary skill in the art were utilized. PCR primers designed to incorporate the desired mutations were also designed with restriction sites to facilitate subsequent cloning steps. Entire segments of Src encoding nucleic acid sequences are deleted from the nucleic acid constructs through PCR amplification techniques based on the known cDNA sequences of chicken, human and the like homologs of Src and subsequent formation of new constructs.

In one embociment of the invention, the 3' PCR primer used to amplify src nucleic acids also encodes for an in-frame sequence. Use of this primer adds a 9E10-myc epitope tag to the carboxyl terminus of the subsequent Src construct.

The following amino acids were added after amino acid 251 of Src to generate vector constructs containing the 9E10-myc epitope tag: VDMEQKLIAEEDLN (SEQ ID NO.: 6). Two separate PCRs were carried out for each construct and similar results were obtained. All mutant constructs constructed by PCR were also sequenced by PCR to confirm predicted DNA sequence of clones. Wild-type and mutated Src cDNAs for use in the expression systems of the present invention are also available from Upstate Biotech Laboratories, Lake Placid, N.Y. which sells avian as well as human src, and several kinase dead and activated mutated forms.

Alternative expression vectors for use in the expressing the Src proteins of the present invention also include adenoviral vectors as described in U.S. Pat. Nos. 4,797,368, 5,173,414, 5,436,146, 5,589,377, and 5,670,488. Alternative methods for the delivery of the Src modulatory proteins include delivery of the Src cDNA with a non-viral vector system as described in U.S. Pat. No. 5,675,954 and delivery of the cDNA itself as naked DNA as described in U.S. Pat. No. 5,589,466. Delivery of constructs of this invention is also not limited to topical application of a viral vector as described in the CAM assay system below. For example, viral vector preparations are also injected intravenously for systemic delivery into the vascular bed. These vectors are also targetable to sites of increased neovascularization by localized injection of a tumor, as an example.

In vitro expressed proteins are also contemplated for delivery thereof following expression and purification of the selected Src protein by methods useful for delivery of proteins or polypeptides. One such method includes liposome delivery systems, such as described in U.S. Pat. Nos. 4,356,167, 5,580,575, 5,542,935 and 5,643,599. Other vector and protein delivery systems are well known to those of ordinary skill in the art for use in the expression and/or delivery of the Src proteins of the present invention.

2. Characterization of the Untreated Chick Chorioallantoic Membrane (CAM)

A. Preparation of the CAM

Angiogenesis can be induced on the chick chorioallantoic membrane (CAM) after normal embryonic angiogenesis has resulted in the formation of mature blood vessels. Angiogenesis has been shown to be induced in response to specific cytokines or tumor fragments as described by Leibovich et al., *Nature*, 329:630 (1987) and Ausprunk et al., *Am. J. Pathol.*, 79:597 (1975). CAMs were prepared from chick embryos for subsequent induction of angiogenesis and inhibition thereof. Ten day old chick embryos were obtained from McIntyre Poultry (Lakeside, Calif.) and incubated at 37° C. with 60% humidity. A small hole was made through the shell at the end of the egg directly over the air sac with the use of a small crafts drill (Dremel, Division of Emerson Electric Co. Racine Wis.). A second hole was drilled on the broad side of the egg in a region devoid of embryonic blood vessels determined previously by candling the egg. Negative pressure was applied to the original hole, which resulted in the CAM (chorioallantoic membrane) pulling away from the shell membrane and creating a false air sac over the CAM. A 1.0 centimeter (cm)×1.0 cm square window was cut through the shell over the dropped CAM with the use of a small model grinding wheel (Dremel). The small window allowed direct access to the underlying CAM.

The resultant CAM preparation was then either used at 6 days of embryogenesis, a stage marked by active neovascularization, without additional treatment to the CAM reflecting the model used for evaluating effects on embryonic neovascularization or used at 10 days of embryogenesis where angiogenesis has subsided. The latter preparation was thus used in this invention for inducing renewed angiogenesis in response to cytokine treatment or tumor contact as described below.

3. CAM Angiogenesis Assay

A. Angiogenesis Induced by Growth Factors

Angiogenesis has been shown to be induced by cytokines or growth factors.

Angiogenesis was induced by placing a 5 millimeter (mm)×5 mm Whatman filter disk (Whatman Filter paper No. 1) saturated with Hanks Balanced Salt Solution (HBSS, GIBCO, Grand Island, N.Y.) or HBSS containing 2 micrograms/milliliter (µg/ml) recombinant basic fibroblast growth factor (bFGF) or vascular endothelial cell growth factor (VEGF) (Genzyme, Cambridge, Mass.) on the CAM of either a 9 or 10 day chick embryo in a region devoid of blood vessels and the windows were latter sealed with tape. Other concentrations of growth factors are also effective at inducing blood vessel growth. For assays where inhibition of angiogenesis is evaluated with intravenous injections of antagonists, angiogenesis is first induced with 1-2 ug/ml bFGF or VEGF in fibroblast growth medium. Angiogenesis was monitored by photomicroscopy after 72 hours.

B. Embryonic Angiogenesis

The CAM preparation for evaluating the effect of angiogenesis inhibitors on the natural formation of embryonic neovasculature is the 6 day embryonic chick embryo as previously described. At this stage in development, the blood vessels are undergoing de novo growth and thus provides a useful system for assessing angiogenesis modulation by the Src proteins of the present invention. The CAM system is prepared as described above with the exception that the assay is performed at embryonic day 6 rather than at day 9 or 10.

4. Modulation of Angiogenesis as Measured in the CAM Assay

To assess the effect of Src proteins on angiogenesis, the following assays were performed on 10 day old chick CAM preparations. Five µg of RCAS constructs prepared as described in Example 1 were transfected into the chicken immortalized fibroblast line, DF-1 (gift of Doug Foster, U. of Minn.). This cell line as well as primary chick embryo fibroblasts were capable of producing virus, however the DF-1 cell line produced higher titres. Viral supernatants were collected from subconfluent DF-1 producer cell lines in serum free CLM media [composition: F-10 media base supplemented with DMSO, folic acid, glutamic acid, and MEM vitamin solution]. Thirty-five ml of viral supernatant were concentrated by ultracentrifugation at 4° C. for 2 hours at 22,000 rpm. These concentrated viral pellets were resuspended in $\frac{1}{100}$ the original volume in serum-free CLM media, aliquoted and stored at −80° C. The titre was assessed by serial dilution of a control viral vector having a nucleotide sequence encoding green fluorescent protein (GFP), referred to as RCAS-GFP, infection on primary chick embryo fibroblasts that were incubated for 48-72 hours. The titres of viral stock that were obtained following concentration routinely exceeded $10^8$ I.u./ml. For the CAM assay using the viral stocks, cortisone acetate soaked Whatman filter disks 6 mm in diameter were prepared in 3 mg/ml cortisone acetate for 30 minutes in 95% ethanol. The disks were dried in a laminar flow hood and then soaked on 20 µl of viral stock per disk for 10 minutes. These disks were applied to the CAM of 9 or 10 day chick embryos and sealed with cellophane tape and incubated at 37° C. for 18-24 hr. Then either mock PBS or growth factors were added at a concentration of 5 µg/ml to the CAM in a 20 µl volume of the appropriate virus stock as an additional boost of virus to the CAM tissue. After 72 hours, the CAMs were harvested and examined for changes in the angiogenic index as determined by double blind counting of the number of branch points in the CAM underlying the disk. For kinase assays, the tissue underlying the disk was harvested in RIPA, homogenized with a motorized grinder and Src immunoprecipitated from equivalent amounts of total protein and subjected to an in vitro kinase assay using a FAK-GST fusion protein as a substrate. For the immunofluorescence studies, CAM tissue underlying the disks were frozen in OCT, a cryopreservative, sectioned at 4 µm, fixed in acetone for 1 minute, incubated in 3% normal goat serum for 1 hour, followed by an incubation in primary rabbit anti-phosphorylated ERK antibody as described previously (Eliceiri et al., *J. Cell Biol.*, 140:1255-1263 (1998), washed in PBS and detected with a fluorescent secondary antibody.

A. Activation of Endogenous Src by bFGF or VEGF

To assess the effects of growth factors on Src activity in modulating angiogenesis, the following assays were performed. Tissue extracts of 10 day old chick CAMs that had been exposed to bFGF or VEGF (2 μg/ml) for 2 hours were lysed. Endogenous Src was immunoprecipitated from equivalent amounts of total protein and subjected to an in vitro immune complex kinase assay using a FAK-GST fusion protein as a substrate, electrophoresed and transferred to nitrocellulose.

The results of the assay are shown in FIG. 5 where the increase in Src activity is evident in the increased density of the gel with either bFGF or VEGF treatment as compared to untreated (mock) samples that are indicative of baseline Src activity in the CAM assay. Both bFGF and VEGF resulted in approximately a 2 fold increase of endogenous Src activity present in the CAM. The above kinase assay blot was also probed with an anti-Src antibody as a loading control for equivalent Src and IgG content.

B. Effect of Retrovirus-Mediated Gene Expression of Src A on Angiogenesis in the Chick CAM The following assay was performed to assess the effect of mutated Src proteins on angiogenesis in the CAM preparation. For the assay, 9 day old chick CAMs were exposed to RCAS-Src A or RCAS-GFP expressing retroviruses or buffer for 72 hour following the protocol described above.

The results of this assay are shown in FIG. 6A where the level of angiogenesis was quantified as described above. Representative photomicrographs (4×) were taken with a stereomicroscope as shown in FIG. 6B. Baseline endogenous Src activity has an angiogenic index of approximately 50. In contrast, CAMs treated with retroviral vector-expressed RCAS-Src A having a point mutation at amino acid residue position 527 from a tyrosine to a phenylalanine resulted in an enhancement (induction) of angiogenesis of an angiogenic index of approximately 90. The enhancement of Src-A mediated angiogenesis is also evident in the photographs shown in FIG. 6B.

C. Retroviral Expression of Src A Activates Vascular MAP Kinase Phosphorylation

The effect of Src A as compared to growth factors VEGF and PMA on vascular MAP kinase phosphorylation was also assessed following the assay procedures described above and herein. Tissue extracts of 10 day old chick CAMs exposed to VEGF or PMA (another mitogen at a comparable concentration) for 30 minutes were compared to those infected with Src A-expressing retrovirus for 48 hours. Src was than immunoprecipitated from equivalent amounts of total protein extract and subjected to an in vitro immune complex kinase assay using a FAK-GST fusion protein as a substrate, electrophoresed and transferred to nitrocellulose.

Figure 7A:
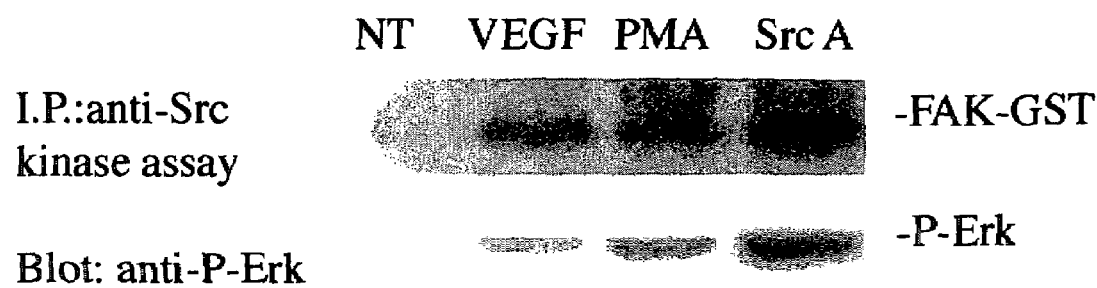
FIG. 7A shows tissue extracts of 10 day-old chick CAMs that had been exposed to VEGF or PMA for 30 minutes or infected with c-Src A retrovirus for 48 hours. NT stands for no treatment. Src was immunoprecipitated from equivalent amounts of total protein extract and subjected to an in vitro immune complex kinase assay using a FAK-GST fusion protein as a substrate, electrophoresed and transferred to nitrocellulose. Aliquots of the above whole tissue lysates were also measured for endogenous ERK phosphorylation by immunoblotting with an anti-phospho-ERK antibody.

The results of this assay are shown in FIG. 7A where untreated CAMs (NT) exhibit base-line endogenous Src-mediated vascular MAP kinase phosphorylation. Both VEGF and PMA resulted in an approximate 2 fold increase over baseline. In contrast, Src A enhanced the activity approximately 5 to 10 fold over that seen with untreated samples.

Figure 7B:
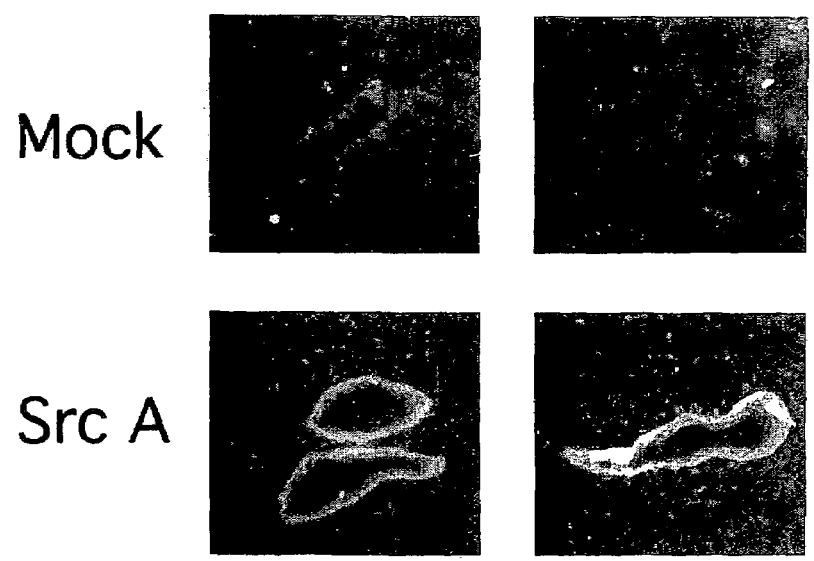
FIG. 7B shows 10 day old CAMs that were infected with either mock RCAS or RCAS containing SRC A. After two days, CAMs were dissected, cryopreserved in OCT and sectioned at 4 μm. Sections were immunostained with an anti-phosphorylated ERK antibody (New England Biolabs), washed and detected with a goat anti-rabbit FITC-conjugated secondary antibody. Florescent images were captured on a cooled-CCD camera (Princeton Inst.)

Aliquots of the above whole tissue lysates were also measured for endogenous ERK phosphorylation by immunoblotting with an anti-phospho-ERK antibody as shown in FIG. 7B. For this assessment, 10 day old CAMs were infected with either mock RCAS or RCAS that expresses SRC A. After two days, CAMs were dissected, cryopreserved in OCT and sectioned at 4 μm. Sections were immunostained with an anti-phosphorylated ERK antibody (New England Biolabs), washed and detected with a goat anti-rabbit FITC-conjugated secondary antibody. Fluorescent images were captured on a cooled-CCD camera (Princeton Inst.). The photomicrographs indicate enhanced immunofluorescence with Src A-treated preparations compared to mock controls.

D. Selective Requirement for Src Activity During VEGF, but Not bFGF-Induced Angiogenesis To assess the effect of Src modulatory activity on growth factor induced angiogenesis, the following assays were performed. Nine day old chick CAMs were exposed to the retroviral vector preparation that expressed the dominant negative Src mutation referred to as Src 251 or Src K295M as previously described. RCAS-Src 251 or control RCAS-GFP retroviruses or buffer CAMS were treated for 20 hours and then incubated for an additional 72 hours in the presence or absence of bFGF or VEGF.

Figure 8A:
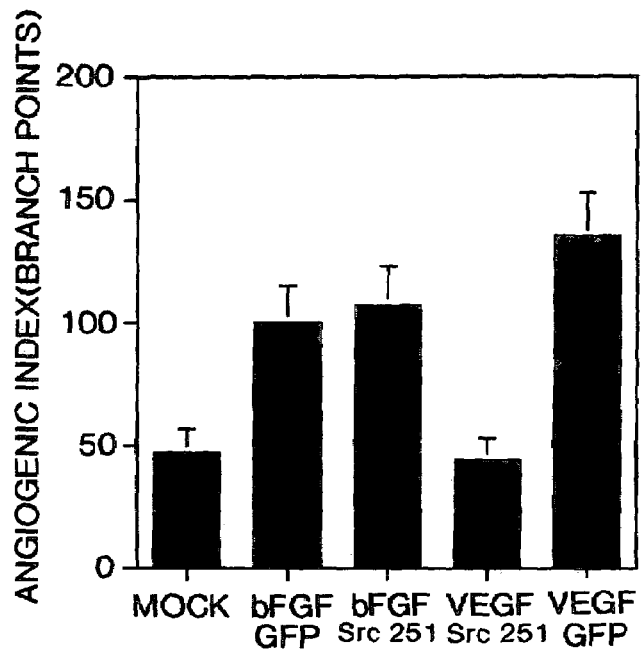
FIG. 8 illustrates the selective requirement for Src activity during VEGF, but not bFGF-induced angiogenesis. Nine day old chick CAMs were exposed to RCAS-Src 251 or control RCAS-GFP retroviruses or buffer for 20 hours and then incubated for an additional 72 hours in the presence or absence of bFGF or VEGF. The level of angiogenesis was quantified FIG. 8A as described above, and representative photomicrographs (6×) were taken with a stereomicroscope as shown in FIG. 8B.
FIG. 8C shows a blot probed with an anti-Src antibody to confirm the expression of Src 251 in transfected cells as compared to mock treatments.
Figure 8B:
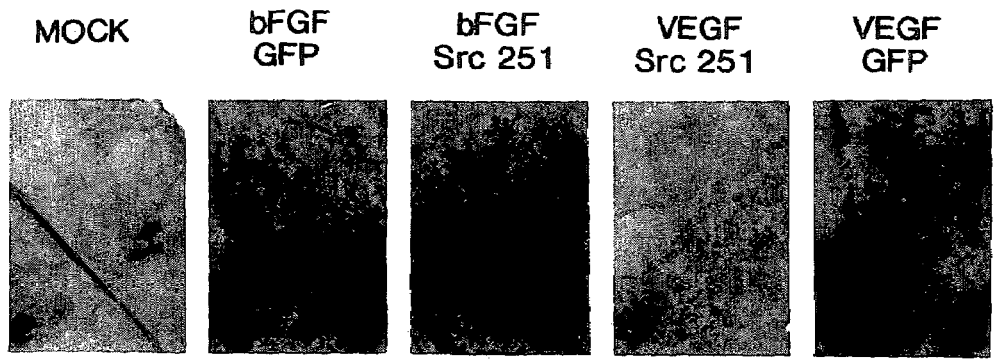
Figure 8C:
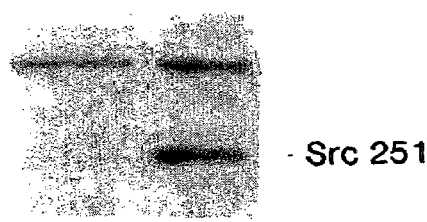

The level of angiogenesis, quantified as described above, is shown in FIG. 8A. Representative photomicrographs (6×), shown in FIG. 8B, were taken with a stereomicroscope. FIG. 8C illustrates a blot probed with an anti-Src antibody to confirm the expression of Src 251 in transfected cells as compared to mock treatments.

The results of the assays described above indicate that both bFGF and VEGF treated CAMS in the presence of RCAS-GFP controls induced angiogenesis over the Src-mediated baseline angiogenesis seen with mock or untreated CAM preparations. The expressed dominant negative mutant Src 251 was effective at inhibiting VEGF-induced angiogenesis back to baseline levels while not effective at inhibiting bFGF-mediated angiogenesis. The photomicrographs shown in FIG. 8B pictorially confirm the data shown in FIG. 8A. Thus, retrovirally expressed Src 251 is an effective angiogenesis inhibitor, when angiogenesis is induced with VEGF.

Applications of the Src proteins of this invention with other angiogenesis models as described in the Examples below are contemplated in the present invention.

5. Regression of Tumor Tissue Growth With Src Modulators as Measured by In Vivo Rabbit Eye Model Assay The effect of Src modulators on growth factor-induced angiogenesis can be observed in naturally transparent structures as exemplified by the cornea of the eye. New blood vessels grow from the rim of the cornea, which has a rich blood supply, toward the center of the cornea, which normally does not have a blood supply. Stimulators of angiogenesis, such as bFGF, when applied to the cornea induce the growth of new blood vessels from the rim of the cornea. Antagonists of angiogenesis, applied to the cornea, inhibit the growth of new blood vessels from the rim of the cornea. Thus, the cornea undergoes angiogenesis through an invasion of endothelial cells from the rim of the cornea into the tough collagen-packed corneal tissue which is easily visible. The rabbit eye model assay therefore provides an in vivo model for the direct observation of stimulation and inhibition of angiogenesis following the implantation of compounds directly into the cornea of the eye.

A. In Vivo Rabbit Eye Model Assay

1) Angiogenesis Induced by Growth Factors

Angiogenesis is induced in the in vivo rabbit eye model assay with growth factors bFGF or VEGF and is described in the following sections.

a. Preparation of Hydron Pellets Containing Growth Factor and Monoclonal Antibodies Hydron polymer pellets containing growth factor are prepared as described by D'Amato, et al., *Proc. Natl. Acad. Sci., USA*, 91:4082-4085 (1994). The individual pellets contain 650 ng of the growth factors separately bound to sucralfate (Carafet, Marion Merrell Dow Corporation) to stabilize the growth factor and ensure its slow release into the surrounding tissue. In addition, hydron pellets are prepared containing a desired Src-expressing retrovirus as previously described. The pellets are cast in specially prepared Teflon pegs that have a 2.5 mm core drilled into their surfaces. Approximately 12 ul of casting material is placed into each peg and polymerized overnight in a sterile hood. Pellets are then sterilized by ultraviolet irradiation. Effects of Src proteins are then assessed as previously described.

6. In Vivo Regression of Tumor Tissue Growth with Src Modulators as Measured by Chimeric Mouse:Human Assay An in vivo chimeric mouse:human model is generated by replacing a portion of skin from a SCID mouse with human neonatal foreskin. The in vivo chimeric mouse:human model is prepared essentially as described in Yan, et al., *J. Clin. Invest.*, 91:986-996 (1993). Briefly, a 2 $cm^2$ square area of skin is surgically removed from a SCID mouse (6-8 weeks of age) and replaced with a human foreskin. The mouse is anesthetized and the hair removed from a 5 $cm^2$ area on each side of the lateral abdominal region by shaving. Two circular graft beds of 2 $cm^2$ are prepared by removing the full thickness of skin down to the fascia. Full thickness human skin grafts of the same size derived from human neonatal foreskin are placed onto the wound beds and sutured into place. The graft is covered with a Band-Aid which is sutured to the skin. Micropore cloth tape is also applied to cover the wound.

The M21-L human melanoma cell line or MDA 23.1 breast carcinoma cell line (ATCC HTB 26; $\alpha_v\beta_3$ negative by immunoreactivity of tissue sections with mAb LM609), are used to form the solid human tumors on the human skin grafts on the SCID mice. A single cell suspension of $5\times10^6$ M21-L or MDA 23.1 cells is injected intradermally into the human skin graft. The mice are then observed for 2 to 4 weeks to allow growth of measurable human tumors.

After a measurable tumor is established, retrovirus preparations of the present invention or PBS is injected into the mouse tail vein. Following a 2-3 week period, the tumor is excised and analyzed by weight and histology. The effect of expressed Src proteins of the present invention on the tumors is then assessed.

7. In Vitro Regression of Human Tumor Tissue Growth with Src Modulators as Measured by CAM Assay Tumor growth depends on angiogenesis (Folkman, 1992; Weidner et al., 1991; Brooks et al., 1994b). In fact, recent reports suggest that tumor growth is susceptible to the anti-angiogenic effects of VEGF receptor antagonists (Kim et al., 1993). Therefore, we examined whether suppression of angiogenesis by delivery of kinase-deleted Src 251 would influence the growth of a human medulloblastoma (DAOY), a highly angiogenic tumor known to produce VEGF and very little bFGF (data not shown).

The 3 and 6 day DAOY medulloblastoma tumor growth assays were performed in the chick CAM essentially as previously described (Brooks et al., 1994). $5\times10^6$ DAOY cells cultured in RPMI 1640 containing 10% fetal calf serum were washed an seeded on the CAM of a 10 day embryo to produce DAOY tumor fragments. After 7 days 50 mg tumor fragments were dissected and reseeded on another 10 day embryo and incubated for another 3 or 6 days with the topical application (25 μl) of either control RCAS-GFP retrovirus, RCAS-Src 251, or mock treatment. Using the whole tissue confocal imaging of infected tumors as a guide we were able to determine that there was significant expression of the RCAS constructs around and within the tumor fragment with this topical approach. Tumor resections and weighing were performed in a double blind manner removing only the easily definable solid tumor mass (Brooks et al., 1994). The wet tumor weights after 3 or 6 days were compared with initial weight and the percent change of tumor weight determined for each group.

These tumors readily grow on the CAM and produces active angiogenesis (FIG. 9) allowing us to selectively target the avian-derived tumor vasculature by using an avian-specific RCAS retrovirus.

Figure 9A:
FIG. 9A is a micrograph that shows human medulloblastoma tumor fragment infected with RCAS-GFP (RCAS-Green Fluorescent Protein) expressing GFP exclusively in the tumor blood vessels (arrowhead) as detected by optical sectioning with a Bio Rad laser confocal scanning microscope (bar=500 μm).
Figure 9B:
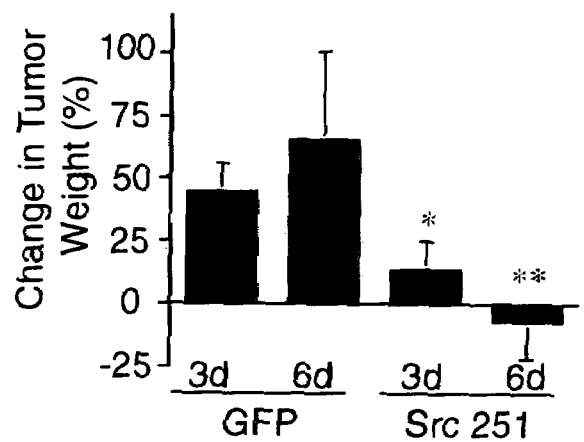
FIG. 9B depicts data from tumors treated with topical application of retrovirus, which were allowed to grow for 3 or 6 days after which they were resected and wet weights determined. Data are expressed as the mean change in tumor weight (from the 50 mg tumor starting weight)+/−SEM of 2 replicates.
Figure 9C:
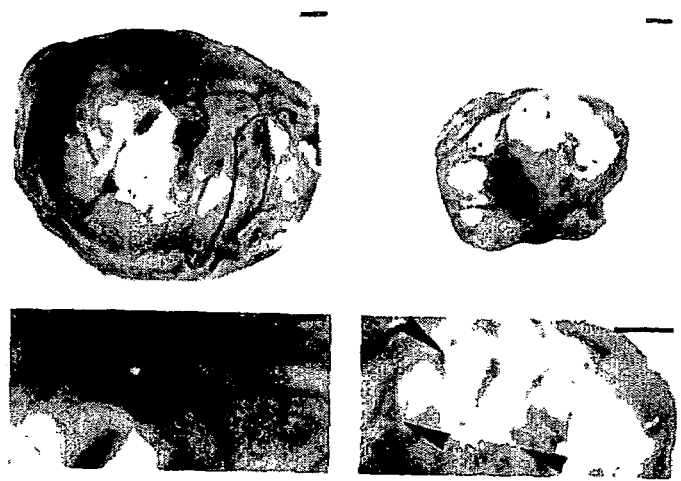
FIG. 9C depicts in representative micrographs, medulloblastoma tumors surgically removed from the embryos (bar=350 μm). The lower panels are high magnification views of each tumor showing the vasculature of each tumor in detail (bar=350 μm). The arrowhead indicates blood vessel disruption in RCAS-Src251-treated tumors.

FIG. 9 depicts results that show retroviral delivery of RCAS-Src 251 to human tumors growing on the chick CAM reverses tumor growth. FIG. 9A shows human medulloblastomas that were grown on the CAM of chick embryos as described above. Retrovirus containing RCAS-GFP or RCAS-Src 251 was topically applied to preestablished tumors of greater than 50 mg. A representative micrograph of a medulloblastoma tumor fragment infected with RCAS-GFP expressing GFP reveals exclusive expression in the tumor blood vessels (arrowhead) as detected by optical sectioning with a Bio Rad laser confocal scanning microscope (bar=500 μm). FIG. 9B shows results from tumors treated as above that were allowed to grow for 3 or 6 days after which they were resected and wet weights determined. Data are expressed as the mean change in tumor weight (from the 50 mg tumor starting weight)+/−SEM of 2 replicates. RCAS-Src 251 had a significant impact on tumor growth after 3 days (*, P<0.002) and 6 days (**, P<0.05). FIG. 9C shows representative stereomicrographs of medulloblastoma tumors surgically removed from the embryos were taken with an Olympus stereomicroscope (bar=350 μm). (Lower panel) A high magnification micrograph of each tumor showing the vasculature of each tumor in detail (bar=350 μm). The arrowhead indicates blood vessel disruption in RCAS-Src251-treated tumors.

The results show that delivery of RCAS containing Src 251 to preestablished medulloblastomas resulted in selective viral expression in the tumor-associated blood vessels (FIG. 9A) and this ultimately led to the regression of these tumors within the span of six days (FIG. 9B). Importantly, the tumor-associated blood vessels in animals treated with virus containing Src 251 were severely disrupted and fewer in number compared to the tumor vessels in control animals (FIG. 9C). The fact that RCAS-GFP infected tumors showed GFP localization only in the tumor vasculature suggests that the anti-tumor effects observed with retrovirally delivered Src 251 were due to its anti-angiogenic properties.

The foregoing examples and the accompanying description are illustrative, and are not be taken as limiting. The present invention also is not to be limited in scope by the cell line deposited, since the deposited embodiment is intended as a single illustration of one aspect of the invention. Any cell line that is functionally equivalent is within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. A method for inhibiting angiogenesis in a tissue associated with a disease condition comprising administering to said tissue a pharmaceutical composition comprising an inactive human c-Src protein selected from the group consisting of: (a) Src 251, which is a polypeptide consisting of residues 1-251 of human c-Src (SEQ ID NO: 5); and (b) Src K295M, which is a polypeptide consisting of SEQ ID NO: 5 in which the lysine residue at position 295 is replaced by a methionine residue.

2. The method of claim 1 wherein said tissue is inflamed and said condition is arthritis or rheumatoid arthritis.

3. The method of claim 1 wherein said tissue is a solid tumor or solid tumor metastasis.

4. The method of claim 3 wherein said administering is conducted in conjunction with chemotherapy.

5. The method of claim 1 wherein said tissue is retinal tissue and said condition is retinopathy, diabetic retinopathy or macular degeneration.

6. The method of claim 1 wherein said tissue is at the site of coronary angioplasty and said tissue is at risk for restenosis.

7. The method of claim 1 wherein said administering comprises intravenous, transdermal, intrasynovial, intramuscular, or oral administration.

8. The method of claim 1 wherein said administering comprises a single dose intravenously.

9. The method of claim 1 wherein said pharmaceutical composition further comprises a liposome.

10. The method of claim 1 wherein said inactive Src protein is Src 251.

* * * * *

UNITED STATES PATENT AND TRADEMARK OFFICE
CERTIFICATE OF CORRECTION

PATENT NO. : 7,585,841 B2  Page 1 of 1
APPLICATION NO. : 11/230995
DATED : September 8, 2009
INVENTOR(S) : Cheresh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this

Fourteenth Day of September, 2010

David J. Kappos
*Director of the United States Patent and Trademark Office*